US009428765B2

(12) United States Patent
Anderson et al.

(10) Patent No.: US 9,428,765 B2
(45) Date of Patent: *Aug. 30, 2016

(54) CORN PLANT AND SEED CORRESPONDING TO TRANSGENIC EVENT MON89034 AND METHODS FOR DETECTION AND USE THEREOF

(71) Applicant: Monsanto Technology LLC, St. Louis, MO (US)

(72) Inventors: Heather M. Anderson, Wildwood, MO (US); Jennifer R. Reyes, New London, CT (US); Jeanna R. Groat, St. Peters, MO (US); Scott C. Johnson, Wildwood, MO (US); Rebecca A. Kelly, South Kingstown, RI (US); John Korte, Westerly, RI (US); James F. Rice, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 322 days.

This patent is subject to a terminal disclaimer.

(21) Appl. No.: 14/078,275

(22) Filed: Nov. 12, 2013

(65) Prior Publication Data

US 2014/0189911 A1 Jul. 3, 2014

Related U.S. Application Data

(60) Division of application No. 13/114,022, filed on May 23, 2011, now Pat. No. 8,581,047, which is a continuation of application No. 11/753,574, filed on May 25, 2007, now Pat. No. 8,062,840.

(60) Provisional application No. 60/808,834, filed on May 26, 2006.

(51) Int. Cl.
    *C12N 15/82* (2006.01)
    *A01H 5/10* (2006.01)
    *C12Q 1/68* (2006.01)

(52) U.S. Cl.
    CPC ............. *C12N 15/8286* (2013.01); *A01H 5/10* (2013.01); *C12Q 1/6895* (2013.01)

(58) Field of Classification Search
    None
    See application file for complete search history.

(56) References Cited

U.S. PATENT DOCUMENTS

| 5,055,294 A | 10/1991 | Gilroy |
| 5,128,130 A | 7/1992 | Gilroy et al. |
| 5,338,544 A | 8/1994 | Donovan |
| 5,362,865 A | 11/1994 | Austin |
| 5,378,619 A | 1/1995 | Rogers |
| 5,500,365 A | 3/1996 | Fischhoff et al. |
| 5,689,052 A | 11/1997 | Brown et al. |
| 5,717,084 A | 2/1998 | Herrera-Estrella et al. |
| 5,728,925 A | 3/1998 | Herrera-Estrella et al. |
| 6,063,601 A | 5/2000 | Herrera-Estrella et al. |
| 6,107,279 A | 8/2000 | Estruch et al. |
| 6,130,366 A | 10/2000 | Herrera-Estrella et al. |
| 6,180,774 B1 | 1/2001 | Brown et al. |
| 6,489,542 B1 | 12/2002 | Corbin et al. |
| 6,713,259 B2 | 3/2004 | Levine |
| 6,868,634 B2 | 3/2005 | Parker |
| 6,962,705 B2 | 11/2005 | Malvar et al. |
| 7,064,249 B2 | 6/2006 | Corbin et al. |
| 7,223,907 B2 | 5/2007 | Huber et al. |
| 7,700,830 B2 | 4/2010 | Corbin et al. |
| 7,858,764 B1 | 12/2010 | Huber et al. |
| 8,030,542 B2 | 10/2011 | Corbin et al. |
| 8,034,997 B2 | 10/2011 | Bogdanova et al. |
| 8,062,840 B2 | 11/2011 | Anderson et al. |
| 8,581,047 B2 * | 11/2013 | Anderson ................ A01H 5/10 800/265 |
| 2004/0034888 A1 | 2/2004 | Liu et al. |
| 2004/0093637 A1 | 5/2004 | Malvar et al. |
| 2004/0172671 A1 | 9/2004 | Ali et al. |
| 2011/0143346 A1 | 6/2011 | Huber et al. |
| 2011/0307978 A1 | 12/2011 | Bogdanova et al. |

FOREIGN PATENT DOCUMENTS

| CN | 1393561 A | 1/2003 |
| EP | 0385962 | 9/1990 |
| EP | 1103616 A2 | 5/2001 |
| WO | WO 95/06730 | 3/1995 |
| WO | WO 95/24492 | 9/1995 |
| WO | WO 95/24493 | 9/1995 |
| WO | WO 95/30752 | 11/1995 |
| WO | WO 95/30753 | 11/1995 |

(Continued)

OTHER PUBLICATIONS

GenBank Accession No. AF034854, dated Dec. 19, 1997.
GenBank Accession No. AF034855, dated Aug. 18, 1999.
GenBank Accession No. AF035413, dated Mar. 5, 1999.
GenBank Accession No. AF035773, dated Dec. 5, 1997.
GenBank Accession No. AF039887, dated Nov. 7, 1998.
GenBank Accession No. AF039888, dated Nov. 7, 1998.
GenBank Accession No. AF117204, dated Jan. 11, 2000.
GenBank Accession No. AF242881, dated Dec. 22, 2006.
GenBank Accession No. AF458479, dated Feb. 22, 2002.
GenBank Accession No. AH006976, dated Nov. 7, 1998.

(Continued)

*Primary Examiner* — Anne Kubelik
(74) *Attorney, Agent, or Firm* — Dentons US LLP; Carine M. Doyle, Esq.; T. K. Ball, Esq.

(57) ABSTRACT

The present invention provides a transgenic corn event MON89034, and cells, seeds, and plants comprising DNA diagnostic for the corn event. The invention also provides compositions comprising nucleotide sequences that are diagnostic for said corn event in a sample, methods for detecting the presence of said corn event nucleotide sequences in a sample, probes and primers for use in detecting nucleotide sequences that are diagnostic for the presence of said corn event in a sample, growing the seeds of such corn event into corn plants, and breeding to produce corn plants comprising DNA diagnostic for the corn event.

6 Claims, 1 Drawing Sheet

(56) References Cited

FOREIGN PATENT DOCUMENTS

| WO | WO 98/22595 | 5/1998 |
|---|---|---|
| WO | WO 99/23232 | 5/1999 |
| WO | WO 00/26371 | 5/2000 |
| WO | WO 00/32800 | 6/2000 |
| WO | WO 02/14517 | 2/2002 |
| WO | WO 02/15701 | 2/2002 |
| WO | WO 02/100163 | 12/2002 |
| WO | WO 03/093484 | 11/2003 |
| WO | WO 2004/020636 | 3/2004 |
| WO | WO 2004/099447 | 11/2004 |
| WO | WO 2005/103301 | 11/2005 |
| WO | WO 2006/039376 | 4/2006 |

OTHER PUBLICATIONS

GenBank Accession No. AJ506356, Aug. 1, 2007.
GenBank Accession No. AY096759, dated Aug. 13, 2002.
GenBank Accession No. AY096762, dated Aug. 14, 2002.
GenBank Accession No. AY141042, dated Sep. 10, 2002.
GenBank Accession No. AY218787, dated Apr. 21, 2003.
GenBank Accession No. AY234331, dated Oct. 12, 2005.
GenBank Accession No. AY456904, dated Nov. 25, 2003.
GenBank Accession No. AY529716, dated Mar. 8, 2004.
GenBank Accession No. AY529717, dated Mar. 8, 2004.
GenBank Accession No. EF192606, dated Jan. 23, 2007.
GenBank Accession No. EU161570, dated Dec. 7, 2007.
GenBank Accession No. EU161573, dated Dec. 7, 2007.
GenBank Accession No. EU161576, dated Oct. 24, 2007.
GenBank Accession No. M14480, dated Apr. 26, 1993.
GenBank Accession No. M14762, dated Apr. 21, 1996.
GenBank Accession No. M80605, dated Apr. 26, 1993.
GenBank Accession No. M80607, dated Apr. 24, 1996.
GenBank Accession No. U19620, dated Sep. 11, 1996.
GenBank Accession No. U43674, dated Aug. 3, 1998.
GenBank Accession No. U48718, dated Oct. 31, 1996.
GenBank Accession No. U60011, dated Jun. 3, 1998.
GenBank Accession No. X04784, dated Sep. 12, 1993.
Adamczyk et al., "Evaluation of Bollgard II (cv. DP50BII) in the Mississippi Delta: Field Efficacy Against Various Lepidoptera While Profiling Season-Long Expression of Cry1Ac and Cry2Ab," *Proceedings of the Beltwide Cotton Conference* 2:835-837, 2001.
Akin et al., "Field Efficacy of Cotton Expressing Two Insecticidal Proteins of Bacillus Thuringiensis," *Proceedings of the Beltwide Cotton Conference* 2:1041-1043, 2001.
Amendment Under 37 C.F.R. §1.312 for U.S Appl. No. 13/114,026 dated Oct. 24, 2012.
APHIS Petition No. 00-342-01P, CBI Deleted Version, 2000.
APHIS Petition No. 06-CR-166U, CBI Deleted Version, Oct. 24, 2006.
APHIS Response to Petition No. 06-298-01p, Jul. 15, 2008.
Armstrong et al., "Factors affecting PEG-mediated stable transformation of maize protoplasts," *Plant Cell Rep.* 9:335-339, 1990.
Bartsch et al., "Lessons we learn from ecological biosafety research," *J. Biotech.* 98:71-77, 2002.
Biopesticide Registration Action Document, "Bacillus thuringiensis Cry1A.105 and Cry2Ab2 Insecticidal Proteins and the Genetic Material Necessary for Their Production in Corn," *U.S. Environmental Protection Agency*, 2010.
Biotradestatus database search results for regulatory and market status of corn plants including single Bt events and stacks across all companies. Accessed at www.biotradestatus.com on Jan. 31, 2013.
Chambers et al., "Isolation and characterization of a novel insecticidal crystal protein gene from *Bacillus thuringiensis* subsp. *Aizawai*," *J. Bacteriol.* 173:3966-3976, Jul. 1991.
Crickmore et al., "Revision of the Nomenclature for the *Bacillus thuringiensis* Pesticidal Crystal Proteins," *Microbiology and Molecular Biology Reviews* 807-813, 1998.

Diehn et al., "Problems that can limit the expression of foreign genes in plants: Lessons to be learned from B.t. toxin genes," *Genetic Engineering; J. K. Setlow, Ed., Plenum Press* (New York, NY) 18:83-99 1996.
Directive 2001/18/EC of the European Parliament and of the Council, *Official Journal of the European Communities* 1-38, 2001.
Dively et al., "Impact of Transgenic VIP3A×Cry1Ab Lepidopteran-resistant Field Corn on the Nontarget Arthropod Community," *Environmental Entomology*, 34(5):1267-1291, 2005.
Dow Agrosciences LLC, "Agronomic Assessment and Seed Increase of GM Cotton Expressing Insecticidal Genes from *Bacillus thuringiensis*," Application for License DIR 040/2003, p. 28 at Appendix 2, 2003.
Drury et al., "Composition of Forage and Granin from Second-Generation Insect-Protected corn MON 89034 is Equivalent to that of Conventional Corn (*Zea mays* L.)," *Journal of Agricultural and Food Chemistry* 56:4623-4630. 2008.
Estrategia Nacional de Biodiversidad, *Ministerio de Desarrollo Sostenible y Planificación* 1-191, 2001, Bolivia.
Extoxnet, Extension Toxicology Network, "*Bacillus thuringiensis*," pp. 1-7, 1994.
*Federal Register* 66(55):15867-15868, 2001.
*Federal Register* 73(143):43202-43203, Jul. 24, 2008.
Final Office Action regarding U.S. Appl. No. 11/801,114, dated Aug. 26, 2009.
GenBank Accession No. AL760295, dated Apr. 1, 2004.
GenBank Accession No. BX290235, dated Apr. 2, 2004.
GenBank Accession No. BX660949, dated Apr. 4, 2004.
GenBank Accession No. BX660950, dated Apr. 4, 2004.
GenBank Accession No. BX894239, dated Apr. 5, 2004.
Gould et al., "Initial frequency of alleles for resistance to *Bacillus thuringiensis* toxins in field populations of *Heliothis virescens*," *Proc. Natl. Acad. Sci.* 94:3519-3523, 1997.
Halpin et al., "Gene stacking in transgenic plants—the challenge for 21st century plant biotechnology," *Plant Biotechnology Journal* 3:141-155, 2005.
Herman et al., "Compositional equivalency of Cry1f corn event TC6275 and conventional corn (*Zea may* L.)," *J. Agric. Food Chem.* 52(9):2726-2734, 2004.
Hernandez et al., "A specific real-time quantitative PCR detection system for event MON810 in maize yieldgard based on the 3'-transgenic integration sequence," *Transgenic Res.* 12(2):179-189, 2003.
Hilbeck et al., "Toxicity of *Bacillus thuringiensis* Cry1Ab toxin to the Predator *Chrysoperia carnea* (Neuroptera: Chrysopidae)," *Environ. Entomol.* 27(5):1255-1263, 1998.
Honée et al., "The C-terminal domain of the toxic fragment of a *Bacillus thuringiensis* crystal protein determines receptor binding," *Mol. Microbiol.* 5(11):2799-2806, Nov. 1991.
Informe De Greenpeace, "*Riesgos para la salud, el medio ambiente y la agricultura del maiz transgénico de Novartis* (Risks for health, the environment, and agriculture of Novartis transgenic corn)," pp. 1-11, 1999.
Jackson et al., "Efficacy of Bollgard and Bollgard II Cottons Against Bollworm, *Helicoverpa Zea (Boddie)* in Field and Greenhouse Studies," *Proceedings of the Beltwide Conference* 2:815-819, 2001.
Kay et al., "Duplication of CaMV 35S Promoter Sequences Creates a Strong Enhancer for Plant Genes," *Science* 236:1299-1302, 1987.
Kota et al., "Overexpression of the *Bacillus thuringiensis* (Bt) Cry2Aa2 protein in chloroplasts confers resistance to plants against susceptible and Bt-resistant insects," *PNAS, USA* 96:1840-1845, 1999.
Koziel et al., "Field Performance of Elite Transgenic Maize Plants Expressing an Insecticidal Protein Derived from *Bacillus thuringiensis*," *Bio/Technology* 11:194-200, 1993.
Koziel et al., "Optimizing expression of transgenes with an emphasis on post-transcriptional events," *Plant Mol. Biol.* 32:393-405, 1996.
Lee et al., "Location of a *Bombyx mori* receptor binding region on *Bacillus thuringiensis* delta-endotoxin," *J. Biol. Chem.* 15(5):3115-3121, Feb. 1992.
Lee et al., "The Mode of Action of the *Bacillus thuringiensis* Vegetative Insecticidal Protein Vip3A Differs from that of Cry1Ab δ-Endotoxin" *Appl. Environ. Microbiol.* 69:4648-4657, 2003.

(56) References Cited

OTHER PUBLICATIONS

Liu et al., "Impact of Transgenic Indica Rice with a Fused Gene of cry1Ab/cry1Ac on the Rice Paddy Anthropod Community," *Acta Entomological Sinica* 46(4) 454-465, 2003.
Lowe et al., "A computer program for selection of oligonucleotide primers for polymerase chain reactions," *Nucleic Acid Research* 18(7):1757-1761, 1990.
MacIntosh et al., "Specificity and Efficacy of Purified *Bacillus thuringiensis* Proteins against Agronomically Important Insects," *J. Invert. Pathol.* 56:258-266, 1990.
Macrea et al., "Laboratory and Field Evaluations of Transgenic Soybean Exhibiting High-Dose Expression of a Synthetic *Bacillus thuringiensis* Cry1A Gene for Control of Lepidoptera" *J. Econ. Entomol.* 98(2):577-587 2005.
Martin-Orue et al., "Degradation of transgenic DNA from genetically modified soy and maize in human intestinal simulations," *British J. Nutrition* 87(6):533-542, 2002.
Mattilla et al., "Response to Danaus plexipuss to pollen of two new Bt corn events via laboratory bioassay," *Entomologia experimentalis et Applicata* 116(1):31-41, 2005.
McCride et al., "Amplification of a Chimeric *Bacillus* Gene in Chloroplasts Leads to an Extraordinary Level of an Insecticidal Protein in Tobacco," *Biotechnology* 13:362-365 1995.
McGaughey et al., "Managing Insect Resistance to *Bacillus thuringiensis* Toxins," *Science* 258:1451-1455, 1993.
Mercola, "First Super Weeds, Now Super Insects—Thanks to Monsanto," *Nation of Change* 1-7, 2013.
New England BioLabs Inc., 1998/99 Catalog, *Nucleic Acids, Linkers and Primers* pp. 121 and 284.
Norman et al., "Performance of Bollgard II Cotton Against Lepidopterous Pests in the Lower Rio Grande Valle of Texas," *Proceedings of the Beltwide Conference* 2:833-835, 2001.
Nucleic Acid Sequences Search Report, Result 11, for SEQ ID No. 3, in U.S. Appl. No. 11/753,574 Office Action dated May 26, 2010.
Nucleic Acid Sequences Search Report, Result 2, for SEQ ID No. 5(3500-4000), in U.S. Appl. No. 11/753,574 Office Action dated May 26, 2010.
Nucleic Acid Sequences Search Report, Result 3, for SEQ ID No. 1, in U.S. Appl. No. 11/753,574 Office Action dated May 26, 2010.
Nucleic Acid Sequences Search Report, Result 5, for SEQ ID No. 5(3500-4000), in U.S. Appl. No. 11/753,574 Office Action dated May 26, 2010.
Nucleic Acid Sequences Search Report, Result 9, for SEQ ID No 4, in U.S. Appl. No. 11/753,754 Office Action dated May 26, 2010.
Office Action issued in Australian Application No. 2007267586 on Aug. 2, 2011.
Office Action issued in Bolivian Application No. SP-270177 dated Apr. 5, 2013.
Office Action issued in Bolivian Patent Application No. SP-270177 on Oct. 8, 2012.
Office Action issued in European Application No. 07797736.1 on Jul. 6, 2011.
Perlak et al., "Genetically improved potatoes: protection from damage by Colorado potato beetles," *Plant Mol. Biol.* 22:313-321, 1993.
Perlak et al., "Insect Resistant Cotton Plants," *Biotechnology* 8(10):939-943, 1990.
Porcar et al., "Molecular and insecticidal characterization of a *Bacillus thuringiensis* strain isolated during a natural epizootic," *J. Applied Microbiology* 89:309-316, 2000.
Response to Office Action dated Mar. 20, 2012 for U.S. Appl. No. 13/114,026 dated Jul. 20, 2012.
Rosso et al., "An Arabidopsis thaliana T-DNA mutagenized population (GABI-Kat) for flanking sequence tag-based reverse genetics," *Plant Mol. Biol.* 53(1-2):247-259.
Rousch "Managing Pests and Their Resistance to *Bacillus thuringiensis*: Can Transgenic Crops be Better Than Sprays?" *Biocontrol Sci. Technol.* 4:501-516, 1994.
Schnepf et al., "Specificity-determining regions of lepidopteran-specific insecticidal protein produced by *Bacillus thuringiensis,*" *J. BioL Chem.* 265(34):20923-20930, Dec. 1990.
Seed Treatments and Traits: Availability, and What's in the Package, LSU AgCenter Research & Extension, downloaded from the Internet on Sep. 20, 2013, http://www.laca1.org/Presentations/2011/Multi%20Crop%20Management%20-%20Rogers%20Leonard%20LSU%20AgCenter.pdf.
Smith et al., "Antisense RNA inhibition of polygalacturonase gene expression in transgenic tomatoes," *Nature* 334:724-726, 1988.
Stam et al., "The Silence of Genes in Transgenic Plants," *Ann. Bot.* 79:3-12, 1997.
Stewart et al., "Impact of Bt Cottons Expressing One or Two Insecticidal Proteins of Bacillus Thuringiensis Berliner on Growth and Survival of Noctuid (*Lepidoptera*) Larvae," *Journal of Economic Entomology* 94(3):752-760, 2001.
Supplemental Response in Light of Examiner's Initiated Interview on Aug. 17, 2012 for U.S. Appl. No. 13/114,026 dated Aug. 20, 2012.
Tapp et al., "Insecticidal Activity of the Toxins from *Bacillus thuringiensis* subspecies *kurstaki* and *tenebrionis* Adsorbed and Bound on Pure and Soil Clays," *Appl. Environ. Microbiol.* 61(5):1786-1790, 1995.
Terminal Disclaimers for U.S. Appl. No. 13/114,026 dated Jul. 20, 2012.
Tu et al., "Expression and Function of a Hybrid *Bt* Toxin Gene in Transgenic Rice Conferring Resistance to Insect Pest," *Plant Biotechnol.* 15(4):195-203, Jun. 2000.
USPTO; Non-final Office Action for U.S. Appl. No. 12/064,875 dated Oct. 21, 2010.
USPTO; Response to Office Action for U.S. Appl. No. 12/064,875 dated Apr. 8, 2011.
USPTO; Notice of Allowance for U.S. Appl. No. 12/064,875 dated Jun. 3, 2011.
USPTO; Non-final Office Action for U.S. Appl. No. 13/114,026 dated Mar. 20, 2012.
USPTO; Notice of Allowance for U.S. Appl. No. 13/114,026 dated Aug. 29, 2012.
Van Frankenhuyzen, "Insecticidal Activity of *Bacillus thuringiensis* crystal proteins" *J. Invert. Pathol.* 101:1-16, Jul. 1997.
Van Pelt-Verkuil et al., "Principles and Technical Aspects of PCR Amplification," *Springer* 1-314, 2007.
Wang et al., "Expression of two insect resistant genes cryIA (bandc) GNA in transgenic tobacco plants results in added protection against both cotton bollworm and aphids," *Chinese Sci. Bull* 44:2051-2058, 1999.
Widner et al., "Location of the Dipteran Specificity Region in a Lepidopteran-Dipteran Crystal Protein from *Bacillus thuringiensis,*" *J. Bacteriol.* 172:2826-2832, 1990.
Widner et al., "Two Highly Related Insecticidal Crystal Proteins of *Bacillus thuringiensis* subsp. *kurstaki* Possess Different Host Range Specificities," *J. Bacteriol.* 171:965-974, 1989.
Wikipedia; http://en.wikipedia.org/wiki/Spodoptera; 2011.
Wilson et al., "Yield, Yield Components, and Fiber Properties of Insect-Resistant Cotton Lines Containing a *Bacillus thuringiensis* Toxin Gene," *Crop Science* 34:38-41, 1994.
Windels et al., "Development of a Line Specific GMO Detection Method: A Case Study," *Med. Fac. Landbouww. Univ. Gent.* 64(5B): 459-462, 1999.
Wong et al., "*Arabidopsis thaliana* small subunit leader and transit peptide enhance The expression of *Bacillus thuringiensis* proteins in transgenic plants," *Plant Mol. Biol.* 20:81-93,1992.
Zhao et al.,"Transgenic plants expressing two *Bacillus thuringiensis* toxins delay insect resistance evolution," *Nature Biotechnol.*, 21:1493-1497, 2003.

\* cited by examiner

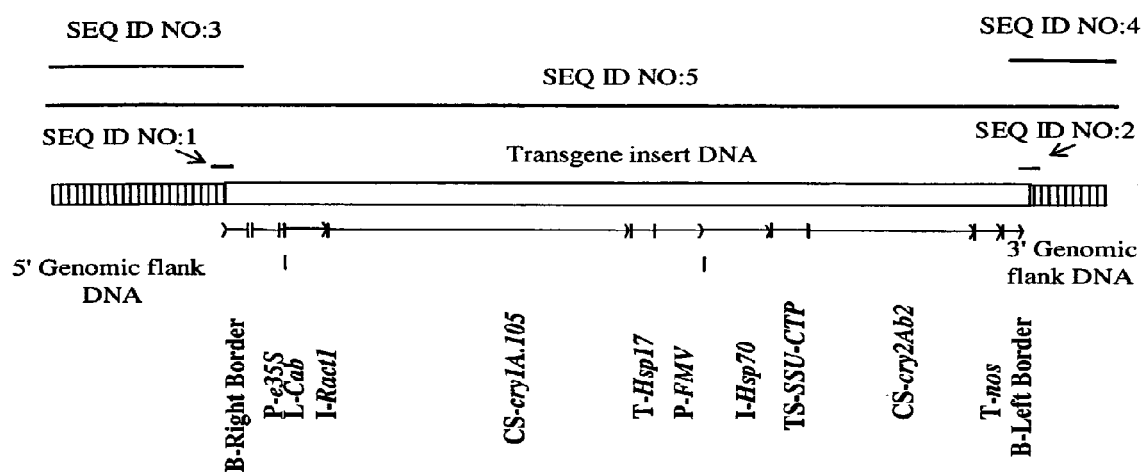

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial
<220> FEATURE:
<223> OTHER INFORMATION: 5' FLANKING GENOME SEQUENCE AND INSERTED DNA
      JUNCTION; corresponding to SEQ ID NO:5 at 2051-2071

<400> SEQUENCE: 1
aatgagtatg atggatcagc a                                                21

<210> SEQ ID NO 2
<211> LENGTH: 20
<212> TYPE: DNA
<213> ORGANISM: Artificial
<220> FEATURE:
<223> OTHER INFORMATION: 3' FLANKING GENOME SEQUENCE AND INSERTED DNA
      JUNCTION; corresponding to SEQ ID NO:5 at 11295-11314

<400> SEQUENCE: 2
actcattgca tccccggaaa                                                  20

<210> SEQ ID NO 3
<211> LENGTH: 2071
<212> TYPE: DNA
<213> ORGANISM: Artificial
<220> FEATURE:
<223> OTHER INFORMATION: 5' FLANKING GENOME SEQUENCE AND INSERTED DNA
      JUNCTION; corresponding to SEQ ID NO:5 at 1-2071

<400> SEQUENCE: 3
aatatttaaa aatggaagta atactatatt aaaatgattc atgtggaact cctgcgcttc      60
tttttgaagt ttcaaaaggg agctttcagg gtcgcttaga gtttgtttgg ttggaaatac    120
aagcgaaaag agagctaatg aggggacat ccatattttc tatggtgttt gaataagagt     180
cacgcgggaa taagatgaac accgaaacaa ttttttttgta gctacgtggt tccaaaaaat    240
cgagtagacg gtgtcgcttc cacctcatac tacttcaacc tcaaaccaca catccttacg    300
cgcccgccgg tgtctccgtc gtctcaagtt ctcaacatac ctacacatgt aaccactacc    360
ggtctttgtc atgtttcgaa agaagattac aggtcctcta gaagagagga cgcggggtgg    420
cgagaaagct ggggaagaaa aaggctagta catatgattg gtctgtgaac ctgtgaggtg    480
ggtaggtagg taggtggaga tttttgttaa ctggtgttgt tgacggactc gaacgggggcc    540
```

-continued

```
gggcgtgtgg tgtggctagc tgtggtggtt tgctcgccag ccagccagcc acacatcagc      600
gagcatgcag agcttaagca tgtatgtacg gatcggcttg cttagcggtt aagggtgtgt      660
ttggtttggc ttttggcttt ggcttttgcc ccctaaaagc caaaagccaa ccaagggtgt      720
atttggtttg acttttggct tttgcttttt gtccctaaa agccaaaagc caaacaaagg      780
gttagatcta ggaagcagct ttttctaaaa gctggctttc tcacagtgca aatctgaaag      840 caccctgaa cctgctttta gtggcttttc gaatggaact gtgaaaacat atatcgaaga      900
acttttaacg acttttagtg gtttccacca aacagtttag cttttttaacg gcttacagcc      960 tacaacagct ttttccacag ctcacagccc acagcaactt ttttcacagc cacagcccaa     1020
ccaaacagac cccaaagggc tgaatccagg aagcagcttt ttctaaaagc cgactttctc     1080
gtagtgtaaa actgaaaaca cccctggacc tgcttttagt ggcttttgga tggaactgtg     1140
aaaacatata tcgaagaact tttaacgact tttagtggtt tccaccaaac gatttctagc     1200
tttttaacag cacacagcct acaacagctt ttttcacagc tcacagccca caacaacttt     1260
ttctacagcc acaacccaac caaacggacc ctaaggcggc cgagcgagcg caaagcgtcg     1320
tcagctttga ttgccatgcc atctcctgct ccacttgtct ctctggccgt cgtcagccac     1380
catccaacaa ggccggtgct actggcggct cctaggtaga cgacgacgac gacgacacct     1440
ccaccgttcg ccgccgtcca ctcaccaatc aacacggaac gcccaaaaca cacacacacg     1500
cacgctgggg agggaaaaaa aggcagagac atatgcgtgc gtcgctgcat tattgtacgc     1560
gatcgaatgg catctctctc actctctctc ctccctttat taatctggta ctggctagct     1620
ggtccggcga caccgacgtg tcagctccgt cgcgcgcgtc cgtccgtccg ctggagcgga     1680
cacggaccgc ggcgtctgtc gatcgccggc tcgccgcagc gcagctacct agcacgctca     1740
cgcatgctac actgcctaca cgcacacggc cggcccaaaa cgttccctg ccgcctgccg     1800 gccggctttt ttattattat tggaacatga ggctatttct cctcccacac gggctacgac     1860
gtgagcacga gtactgggat ccccggatcc gccctctctg tccctgctgc tactccagcc     1920
actgaaatgt tgtcagatga aacagcagag ccgatctccg cacggaaacc catgcacggc     1980
cattcaaatt caggtgccca cgtacgtcag ggtgctgctg ctactactat caagccaata     2040
aaaggatggt aatgagtatg atggatcagc a                                    2071
```

<210> SEQ ID NO 4
<211> LENGTH: 914
<212> TYPE: DNA
<213> ORGANISM: Artificial
<220> FEATURE:
<223> OTHER INFORMATION: 3' FLANKING GENOME SEQUENCE AND INSERTED DNA
      JUNCTION; corresponding to SEQ ID NO:5 at 11295-12208

<400> SEQUENCE: 4

```
actcattgca tccccggaaa ttatgttttt ttaaaaacca cggtattata gataccgtgt       60
tattttttga gtattggaaa tttcatttca acccaaagtt tcttcatggc acatctagct      120
tttgcctaat accatgtagg gctacatctt aaaaatctat actactatat taaagctgca      180
ggggtagcct gtctccacct ggttctgcct cgagccaatc taaaccgtcc atctatatcc      240
atcaaatcag caccgtccgg tccgtgcgca cctcctctcc cgctattcag ttgcatactt      300
gcagcaggtt ctccctcctc accatttcct ctgcctcctc tctcgctcac tggtcagatt      360
catcctgcct ctcccgcatg cgctcccctcc ccatgcccg tctcgcacta tcgccacacc      420
tcaccgcggg gagacgaaga cggtggacgc atcctcacct cctccgctag ttgtcgctct      480
```

-continued

| | |
|---|---|
| tccatcctct tcaacaactt ctacataggg agaggcggtt cggcgtcccg acgccgccgc | 540 |
| ttctcccctc cccatggagg acgagaacat cgacctcggc ggcgggggcg atgcctccgc | 600 |
| tctgcataga ggagggttgt agtggcaagc agcaatgcca acaccgaggc gggccaagac | 660 |
| taggcaacaa taggacggca cgcccggttg tcagcgaggt ggcggcatcg tgtgccgcta | 720 |
| ccgaacaaca tctccggcgc tggagtcggt gagttactgc gccacccgga cgccctcaat | 780 |
| gcactgatat ctaccggtc tccatcgccg cccttcctcc cttccctctc cctgtgcctc | 840 |
| cctctcttgc cctctccctt ccaactgctc ccgccccagc cctagcccaa ccacctcccg | 900 |
| cgcagggtca ccaa | 914 |

<210> SEQ ID NO 5
<211> LENGTH: 12208
<212> TYPE: DNA
<213> ORGANISM: Artificial
<220> FEATURE:
<223> OTHER INFORMATION: 5' FLANKING GENOME SEQUENCE PLUS INSERTED DNA
    SEQUENCE PLUS 3' FLANKING GENOME SEQUENCE

<400> SEQUENCE: 5

| | |
|---|---|
| aatatttaaa aatggaagta atactatatt aaaatgattc atgtggaact cctgcgcttc | 60 |
| tttttgaagt ttcaaaaggg agcttttcagg gtcgcttaga gtttgtttgg ttggaaatac | 120 |
| aagcgaaaag agagctaatg aggggacat ccatattttc tatggtgttt gaataagagt | 180 |
| cacgcgggaa taagatgaac accgaaacaa ttttttttgta gctacgtggt tccaaaaaat | 240 |
| cgagtagacg tgtcgcttc cacctcatac tacttcaacc tcaaaccaca catccttacg | 300 |
| cgcccgccgg tgtctccgtc gtctcaagtt ctcaacatac ctacacatgt aaccactacc | 360 |
| ggtctttgtc atgtttcgaa agaagattac aggtcctcta aagagagga cgcggggtgg | 420 |
| cgagaaagct ggggaagaaa aaggctagta catatgattg gtctgtgaac ctgtgaggtg | 480 |
| ggtaggtagg taggtggaga ttttttgttaa ctggtgttgt tgacggactc gaacggggcc | 540 |
| gggcgtgtgg tgtggctagc tgtggtggtt tgctcgccag ccagccagcc acacatcagc | 600 |
| gagcatgcag agcttaagca tgtatgtacg gatcggcttg cttagcggtt aagggtgtgt | 660 |
| ttggtttggc ttttggcttt ggcttttgcc ccctaaaagc caaaagccaa ccaagggtgt | 720 |
| atttggtttg acttttggct tttggctttt gtcccctaaa agccaaaagc caaacaaagg | 780 |
| gttagatcta ggaagcagct ttttctaaaa gctggctttc tcacagtgca aatctgaaag | 840 |
| caccccctgaa cctgctttta gtggcttttc gaatggaact gtgaaaacat atatcgaaga | 900 |
| acttttaacg acttttagtg gtttccacca aacagtttag cttttttaacg gcttacagcc | 960 |
| tacaacagct ttttccacag ctcacagccc acagcaactt ttttcacagc cacagcccaa | 1020 |
| ccaaacagac cccaaagggc tgaatccagg aagcagcttt ttctaaaagc cgactttctc | 1080 |
| gtagtgtaaa actgaaaaca cccctggacc tgcttttagt ggcttttgga tggaactgtg | 1140 |
| aaaacatata tcgaagaact tttaacgact tttagtggtt tccaccaaac gatttctagc | 1200 |
| ttttttaacag cacacagcct acaacagctt ttttcacagc tcacagccca caacaacttt | 1260 |
| ttctacagcc acaacccaac caaacggacc ctaaggcggc cgagcgagcg caaagcgtcg | 1320 |
| tcagctttga ttgccatgcc atctcctgct ccacttgtct ctctggccgt cgtcagccac | 1380 |
| catccaacaa ggccggtgct actggcggct cctaggtaga cgacgacgac gacgacacct | 1440 |
| ccaccgttcg ccgccgtcca ctcaccaatc aacacggaac gcccaaaaca cacacacacg | 1500 |
| cacgctgggg agggaaaaaa aggcagagac atatgcgtgc gtcgctgcat tatttgtacgc | 1560 |

-continued

```
gatcgaatgg catctctctc actctctctc ctcccttat taatctggta ctggctagct    1620
ggtccggcga caccgacgtg tcagctccgt cgcgcgcgtc cgtccgtccg ctggagcgga    1680
cacggaccgc ggcgtctgtc gatcgccggc tcgccgcagc gcagctacct agcacgctca    1740
cgcatgctac actgcctaca cgcacacggc cggcccaaaa gcgttccctg ccgcctgccg    1800
gccggctttt ttattattat tggaacatga ggctatttct cctcccacac gggctacgac    1860
gtgagcacga gtactgggat ccccggatcc gccctctctg tccctgctgc tactccagcc    1920
actgaaatgt tgtcagatga acagcagag ccgatctccg cacggaaacc catgcacggc    1980
cattcaaatt caggtgccca cgtacgtcag ggtgctgctg ctactactat caagccaata    2040
aaaggatggt aatgagtatg atggatcagc aatgagtatg atggtcaata tggagaaaaa    2100
gaaagagtaa ttaccaattt tttttcaatt caaaaatgta gatgtccgca gcgttattat    2160
aaaatgaaag tacattttga taaaacgaca aattacgatc cgtcgtattt ataggcgaaa    2220
gcaataaaca aattattcta attcggaaat ctttatttcg acgtgtctac attcacgtcc    2280
aaatggggc ttagatgaga aacttcacga tttggcgcgc caaagcttgg tcgagtggaa    2340
gctagctttc cgatcctacc tgtcacttca tcaaaaggac agtagaaaag gaaggtggct    2400
cctacaaatg ccatcattgc gataaaggaa aggccatcgt tgaagatgcc tctgccgaca    2460
gtggtcccaa agatggaccc ccacccacga ggagcatcgt ggaaaagaa gacgttccaa    2520
ccacgtcttc aaagcaagtg gattgatgtg atatctccac tgacgtaagg gatgacgcac    2580
aatcccacta tccttcgcaa gaccctctct ctatataagg aagttcattt catttggaga    2640
ggacacgctg acaagctgac tctagcagat cctctagaac catcttccac acactcaagc    2700
cacactattg gagaacacac agggacaaca caccataaga tccaagggag gcctccgccg    2760
ccgccggtaa ccaccccgcc cctctcctct ttctttctcc gttttttttt ccgtctcggt    2820
ctcgatcttt ggccttggta gtttgggtgg gcgagaggcg gcttcgtgcg cgcccagatc    2880
ggtgcgcggg aggggcggga tctcgcggct ggggctctcg ccggcgtgga tccggcccgg    2940
atctcgcggg gaatggggct ctcggatgta gatctgcgat ccgccgttgt tggggagat    3000
gatgggggt ttaaaattc cgccgtgcta aacaagatca ggaagagggg aaaagggcac    3060
tatggtttat attttatat atttctgctg cttcgtcagg cttagatgtg ctagatctt    3120
ctttcttctt tttgtgggta gaatttgaat ccctcagcat tgttcatcgg tagttttct    3180
tttcatgatt tgtgacaaat gcagcctcgt gcggagcttt tttgtaggta gaagtgatca    3240
accatggaca acaacccaaa catcaacgag tgcatcccgt acaactgcct cagcaaccct    3300
gaggtcgagg tgctcggcgg tgagcgcatc gagaccggtt acaccccat cgacatctcc    3360
ctctccctca cgcagttcct gctcagcgag ttcgtgccag cgctggctt cgtcctgggc    3420
ctcgtggaca tcatctgggg catctttggc ccctcccagt gggacgcctt cctggtgcaa    3480
atcgagcagc tcatcaacca gaggatcgag gagttcgcca ggaaccaggc catcagccgc    3540
ctggagggcc tcagcaacct ctaccaaatc tacgctgaga gcttccgcga gtgggaggcc    3600
gaccccacta acccagctct ccgcgaggag atgcgcatcc agttcaacga catgaacagc    3660
gccctgacca ccgccatccc actcttcgcc gtccagaact accaagtccc gctcctgtcc    3720
gtgtacgtcc aggccgccaa cctgcacctc agcgtgctga gggacgtcag cgtgtttggc    3780
cagaggtggg gcttcgacgc cgccaccatc aacagccgct acaacgacct caccaggctg    3840
atcggcaact acaccgacca cgctgtccgc tggtacaaca ctggccgtcc tggacattgt    3900
gtccctcttc ccgaactacg actcccgcac ctacccgatc cgcaccgtgt cccaactgac    3960
```

-continued

```
ccgcgaaatc tacaccaacc ccgtcctgga gaacttcgac ggtagcttca ggggcagcgc    4020
ccagggcatc gagggctcca tcaggagccc acacctgatg acatcctca acagcatcac    4080 tatctacacc gatgcccacc gcggcgagta ctactggtcc ggccaccaga tcatggcctc    4140
cccggtcggc ttcagcggcc ccgagtttac ctttcctctc tacggcacga tgggcaacgc    4200
cgctccacaa caacgcatcg tcgctcagct gggccagggc gtctaccgca ccctgagctc    4260
caccctgtac cgcaggccct tcaacatcgg tatcaacaac cagcagctgt ccgtcctgga    4320
tggcactgag ttcgcctacg gcacctcctc caacctgccc tccgctgtct accgcaagag    4380
cggcacggtg gattccctgg acgagatccc accacagaac aacaatgtgc cccccaggca    4440
gggttttccc cacaggctca gccacgtgtc catgttccgc tccggcttca gcaactcgtc    4500
cgtgagcatc atcagagctc ctatgttctc ttggatacac cgtagtgctg agttcaacaa    4560
catcattgca tccgacagca ttactcaaat acccttggtg aaagcacata cacttcagtc    4620
aggtactact gttgtcagag gtccagggtt tacaggagga gcattcttc gtcgcacaag    4680 tggagaccc tttgcttaca ctattgttaa catcaatggc caattgcccc aaaggtatcg    4740
tgcaagaatc cgctatgcct ctactacaaa tctcaggatc tacgtgactg ttgcaggtga    4800
aaggatcttt gctggtcagt tcaacaagac tatggatacc ggtgaccctt tgacattcca    4860
atcttttagc tacgcaacta tcaacacagc ttttacattc ccaatgagcc agagtagctt    4920
cacagtaggt gctgacactt tcagctcagg gaatgaagtt tacatcgaca ggtttgaatt    4980
gattccagtt actgcaaccc tcgaggctga gtacaacctt gagagagccc agaaggctgt    5040
gaacgccctc tttacctcca ccaatcagct tggcttgaaa actaacgtta ctgactatca    5100
cattgaccaa gtgtccaact tggtcaccta ccttagcgat gagttctgcc tcgacgagaa    5160
gcgtgaactc tccgagaaag ttaaacacgc caagcgtctc agcgacgaga ggaatctctt    5220
gcaagactcc aacttcaaag acatcaacag gcagccagaa cgtggttggg gtggaagcac    5280
cgggatcacc atccaaggag gcgacgatgt gttcaaggag aactacgtca ccctctccgg    5340
aactttcgac gagtgctacc ctacctactt gtaccagaag atcgatgagt ccaaactcaa    5400
agccttcacc aggtatcaac ttagaggcta catcgaagac agccaagacc ttgaaatcta    5460
ctcgatcagg tacaatgcca agcacgagac cgtgaatgtc ccaggtactg gttccctctg    5520
gccactttct gcccaatctc ccattgggaa gtgtggagag cctaacagat gcgctccaca    5580
ccttgagtgg aatcctgact tggactgctc ctgcagggat ggcgagaagt gtgcccacca    5640
ttctcatcac ttctccttgg acatcgatgt gggatgtact gacctgaatg aggacctcgg    5700
agtctgggtc atcttcaaga tcaagaccca agacggacac gcaagacttg caaccttga    5760 gtttctcgaa gagaaaccat tggtcggtga agctctcgct cgtgtgaaga gagcagagaa    5820
gaagtggagg gacaaacgtg agaaactcga atgggaaact aacatcgttt acaaggaggc    5880
caaagagtcc gtggatgctt tgttcgtgaa ctcccaatat gatcagttgc aagccgacac    5940
caacatcgcc atgatccacg ccgcagacaa acgtgtgcac agcattcgtg aggcttactt    6000
gcctgagttg tccgtgatcc ctggtgtgaa cgctgccatc ttcgaggaac ttgagggacg    6060
tatctttacc gcattctcct tgtacgatgc cagaaacgtc atcaagaacg tgacttcaa    6120 caatggcctc agctgctgga atgtgaaagg tcatgtggac gtggaggaac agaacaatca    6180
gcgttccgtc ctggttgtgc ctgagtggga agctgaagtg tcccaagagg ttagagtctg    6240
tccaggtaga ggctacattc tccgtgtgac cgcttacaag gagggatacg gtgagggttg    6300
```

-continued

```
cgtgaccatc cacgagatcg agaacaacac cgacgagctt aagttctcca actgcgtcga    6360
ggaagaaatc tatcccaaca acaccgttac ttgcaacgac tacactgtga atcaggaaga    6420
gtacggaggt gcctacacta gccgtaacag aggttacaac gaagctcctt ccgttcctgc    6480
tgactatgcc tccgtgtacg aggagaaatc ctacacagat ggcagacgtg agaacccttg    6540
cgagttcaac agaggttaca gggactacac accacttcca gttggctatg ttaccaagga    6600
gcttgagtac tttcctgaga ccgacaaagt gtggatcgag atcggtgaaa ccgagggaac    6660
cttcatcgtg gacagcgtgg agcttctctt gatggaggaa taatgagatc tatcgattct    6720
agaaggcctg aattctgcat gcgtttggac gtatgctcat tcaggttgga gccaatttgg    6780
ttgatgtgtg tgcgagttct tgcgagtctg atgagacatc tctgtattgt gtttctttcc    6840
ccagtgtttt ctgtacttgt gtaatcggct aatcgccaac agattcggcg atgaataaat    6900
gagaaataaa ttgttctgat tttgagtgca aaaaaaagg aattagatct gtgtgtgttt    6960
tttggatccc cggggcggcc gcgttaacaa gcttgagctc aggatttagc agcattccag    7020
attgggttca atcaacaagg tacgagccat atcactttat tcaaattggt atcgccaaaa    7080
ccaagaagga actcccatcc tcaaaggttt gtaaggaaga attctcagtc caaagcctca    7140
acaaggtcag ggtacagagt ctccaaacca ttagccaaaa gctacaggag atcaatgaag    7200
aatcttcaat caaagtaaac tactgttcca gcacatgcat catggtcagt aagtttcaga    7260
aaaagacatc caccgaagac ttaaagttag tgggcatctt tgaaagtaat cttgtcaaca    7320
tcgagcagct ggcttgtggg gaccagacaa aaaggaatg gtgcagaatt gttaggcgca    7380
cctaccaaaa gcatctttgc ctttattgca agataaagc agattcctct agtacaagtg    7440
gggaacaaaa taacgtggaa aagagctgtc ctgacagccc actcactaat gcgtatgacg    7500
aacgcagtga cgaccacaaa agaattccct ctatataaga aggcattcat tcccatttga    7560
aggatcatca gatactcaac caatccttct aggatctacc gtcttcggta cgcgctcact    7620
ccgcccctg cctttgttac tgccacgttt ctctgaatgc tctcttgtgt ggtgattgct    7680
gagagtggtt tagctggatc tagaattaca ctctgaaatc gtgttctgcc tgtgctgatt    7740
acttgccgtc ctttgtagca gcaaaatata gggacatggt agtacgaaac gaagatagaa    7800
cctacacagc aatacgagaa atgtgtaatt tggtgcttag cggtatttat ttaagcacat    7860
gttggtgtta tagggcactt ggattcagaa gtttgctgtt aatttaggca caggcttcat    7920
actacatggg tcaatagtat agggattcat attataggcg atactataat aatttgttcg    7980
tctgcagagc ttattatttg ccaaaattag atattcctat tctgttttg tttgtgtgct    8040
gttaaattgt taacgcctga aggaataaat ataaatgacg aaattttgat gtttatctct    8100
gctcctttat tgtgaccata agtcaagatc agatgcactt gttttaaata ttgttgtctg    8160
aagaaataag tactgacagt attttgatgc attgatctgc ttgtttgttg taacaaaatt    8220
taaaaataaa gagtttcctt tttgttgctc tccttacctc ctgatggtat ctagtatcta    8280
ccaactgaca ctatattgct tctctttaca tacgtatctt gctcgatgcc ttctccctag    8340
tgttgaccag tgttactcac atagtctttg ctcatttcat tgtaatgcag ataccaagcg    8400
gcctctagag gatcagcatg gcgcccaccg tgatgatggc ctcgtcggcc accgccgtcg    8460
ctccgttcca ggggctcaag tccaccgcca gcctccccgt cgcccgccgc tcctccagaa    8520
gcctcggcaa cgtcagcaac ggcggaagga tccggtgcat gcaggtaaca aatgcatcct    8580
agctagtagt tctttgcatt gcagcagctg cagctagcga gttagtaata ggaagggaac    8640
tgatgatcca tgcatggact gatgtgtgtt gcccatccca tcccatttcc caaccccaaa    8700
```

```
cgaaccaaaa cacacgtact acgtgcaggt gtggccggcc tacggcaaca agaagttcga      8760
gacgctgtcg tacctgccgc cgctgtcgac cggcgggcgc atccgctgca tgcaggccat      8820
ggacaactcc gtcctgaact ctggtcgcac caccatctgc gacgcctaca acgtcgcggc      8880
gcatgatcca ttcagcttcc agcacaagag cctcgacact gttcagaagg agtggacgga      8940
gtggaagaag aacaaccaca gcctgtacct ggaccccatc gtcggcacgg tggccagctt      9000
ccttctcaag aaggtcggct ctctcgtcgg gaagcgcatc ctctcggaac tccgcaacct      9060
gatctttcca tctggctcca ccaacctcat gcaagacatc ctcagggaga ccgagaagtt      9120
tctcaaccag cgcctcaaca ctgatacect tgctcgcgtc aacgctgagc tgacgggtct      9180
gcaagcaaac gtggaggagt tcaaccgcca agtggacaac ttcctcaacc ccaaccgcaa      9240
tgcggtgcct ctgtccatca cttcttccgt gaacaccatg caacaactgt tcctcaaccg      9300
cttgcctcag ttccagatgc aaggctacca gctgctcctg ctgccactct tgctcaggc      9360 tgccaacctg cacctctcct tcattcgtga cgtgatcctc aacgctgacg agtggggcat      9420
ctctgcagcc acgctgagga cctaccgcga ctacctgaag aactacacca gggactactc      9480
caactattgc atcaacacct accagtcggc cttcaagggc ctcaatacga ggcttcacga      9540
catgctggag ttcaggacct acatgttcct gaacgtgttc gagtacgtca gcatctggtc      9600
gctcttcaag taccagagcc tgctggtgtc cagcggcgcc aacctctacg ccagcggctc      9660
tggtccccaa caaactcaga gcttcaccag ccaggactgg ccattcctgt attcgttgtt      9720
ccaagtcaac tccaactacg tcctcaacgg cttctctggt gctcgcctct ccaacacctt      9780
ccccaacatt gttggcctcc ccggctccac cacaactcat gctctgcttg ctgccagagt      9840
gaactactcc ggcggcatct cgagcggcga cattggtgca tcgccgttca accagaactt      9900
caactgctcc accttcctgc cgccgctgct caccccgttc gtgaggtcct ggctcgacag      9960
cggctccgac cgcgagggcg tggccaccgt caccaactgg caaaccgagt ccttcgagac     10020
cacccttggc ctccggagcg cgccttcac ggcgcgtgga aattctaact acttccccga     10080
ctacttcatc aggaacatct ctggtgttcc tctcgtcgtc cgcaacgagg acctccgccg     10140
tccactgcac tacaacgaga tcaggaacat cgcctctccg tccgggacgc ccggaggtgc     10200
aagggcgtac atggtgagcg tccataacag gaagaacaac atccacgctg tgcatgagaa     10260
cggctccatg atccacctgg cgcccaatga ttacaccggc ttcaccatct ctccaatcca     10320
cgccacccaa gtgaacaacc agacacgcac cttcatctcc gagaagttcg gcaaccaggg     10380
cgactccctg aggttcgagc agaacaacac caccgccagg tacaccctgc gcggcaacgg     10440
caacagctac aacctgtacc tgcgcgtcag ctccattggc aactccacca tcagggtcac     10500
catcaacggg agggtgtaca cagccaccaa tgtgaacacg acgaccaaca atgatggcgt     10560
caacgacaac ggcgcccgct tcagcgacat caacattggc aacgtggtgg ccagcagcaa     10620
ctccgacgtc ccgctggaca tcaacgtgac cctgaactct ggcacccagt cgacctcat      10680 gaacatcatg ctggtgccaa ctaacatctc gccgctgtac tgataggagc tctgatcccc     10740
atgggaattc ccgatcgttc aaacatttgg caataaagtt tcttaagatt gaatcctgtt     10800
gccggtcttg cgatgattat catataattt ctgttgaatt acgttaagca tgtaataatt     10860
aacatgtaat gcatgacgtt atttatgaga tgggttttta tgattagagt cccgcaatta     10920
tacatttaat acgcgataga aaacaaaata tagcgcgcaa actaggataa attatcgcgc     10980
gcggtgtcat ctatgttact agatcgggga tatccccggg gcggccgcgg ggaattcggt     11040
```

```
accaagcttt ggcgcgccaa atcgtgaagt ttctcatcta agcccccatt tggacgtgaa    11100
tgtagacacg tcgaaataaa gatttccgaa ttagaataat ttgtttattg ctttcgccta    11160
taaatacgac ggatcgtaat ttgtcgtttt atcaaaatgt actttcattt tataataacg    11220
ctgcggacat ctacatttt gaattgaaaa aaaattggta attactcttt cttttctcc      11280 atattgacca tcatactcat tgcatccccg gaaattatgt tttttaaaa accacggtat     11340 tatagatacc gtgttatttt ttgagtattg gaaatttcat ttcaacccaa agttcttca     11400 tggcacatct agcttttgcc taataccatg tagggctaca tcttaaaaat ctatactact    11460
atattaaagc tgcaggggta gcctgtctcc acctggttct gcctcgagcc aatctaaacc    11520
gtccatctat atccatcaaa tcagcaccgt ccggtccgtg cgcacctcct ctcccgctat    11580
tcagttgcat acttgcagca ggttctccct cctcaccatt tcctctgcct cctctctcgc    11640
tcactggtca gattcatcct gcctctcccg catgcgctcc ctccccatgc cccgtctcgc    11700
actatcgcca cacctcaccg cggggagacg aagacggtgg acgcatcctc acctcctccg    11760
ctagttgtcg ctcttccatc ctcttcaaca acttctacat agggagaggc ggttcggcgt    11820
cccgacgccg ccgcttctcc cctccccatg gaggacgaga acatcgacct cggcggcggg    11880
ggcgatgcct ccgctctgca tagaggaggg ttgtagtggc aagcagcaat gccaacaccg    11940
aggcgggcca agactaggca acaataggac ggcacgcccg gttgtcagcg aggtggcggc    12000
atcgtgtgcc gctaccgaac aacatctccg gcgctggagt cggtgagtta ctgcgccacc    12060
cggacgccct caatgcactg atatctaccc ggtctccatc gccgccttc ctcccttccc     12120 tctccctgtg cctccctctc ttgccctctc ccttccaact gctcccgccc cagccctagc    12180
ccaaccacct cccgcgcagg gtcaccaa                                       12208
```

<210> SEQ ID NO 6
<211> LENGTH: 22
<212> TYPE: DNA
<213> ORGANISM: Artificial
<220> FEATURE:
<223> OTHER INFORMATION: PORTION OF DNA SEQUENCE INSERTED INTO CORN
      GENOME; corresponding to SEQ ID NO:5 at 2034-2055

<400> SEQUENCE: 6
gccaataaaa ggatggtaat ga                                                22

<210> SEQ ID NO 7
<211> LENGTH: 23
<212> TYPE: DNA
<213> ORGANISM: Artificial
<220> FEATURE:
<223> OTHER INFORMATION: PORTION OF DNA SEQUENCE INSERTED INTO CORN
      GENOME; corresponding to SEQ ID NO:5 at 11345-11367

<400> SEQUENCE: 7 cttttctcc atattgacca tca                                                23

<210> SEQ ID NO 8
<211> LENGTH: 20
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 8
ggtatccctc cagaccagca                                                   20

<210> SEQ ID NO 9
<211> LENGTH: 24
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 9
gtggactcct tctggatgtt gtaa                                              24

<210> SEQ ID NO 10
<211> LENGTH: 21
<212> TYPE: DNA
<213> ORGANISM: Artificial
<220> FEATURE:
<223> OTHER INFORMATION: OLIGONUCLEOTIDE PRIMER SQ652

<400> SEQUENCE: 10
gtcagggtgc tgctgctgct a                                                 21

<210> SEQ ID NO 11
<211> LENGTH: 23
<212> TYPE: DNA
<213> ORGANISM: Artificial
<220> FEATURE:
<223> OTHER INFORMATION: OLIGONUCLEOTIDE PRIMER SQ6524

<400> SEQUENCE: 11
ggtttaagaa ccattttgct ccc                                               23

<210> SEQ ID NO 12
<211> LENGTH: 24
<212> TYPE: DNA
<213> ORGANISM: Artificial
<220> FEATURE:
<223> OTHER INFORMATION: OLIGONUCLEOTIDE SEQUENCE CORRESPONDING TO SEQ
      ID NO:5 AT 2003-2026

<400> SEQUENCE: 12
tacgtcaggg tgctgctgct acta                                              24

<210> SEQ ID NO 13
<211> LENGTH: 24
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 13
atratttycg gggatgcaac caac                                              24

<210> SEQ ID NO 14
<211> LENGTH: 16
<212> TYPE: DNA
<213> ORGANISM: Artificial
<220> FEATURE:
<223> OTHER INFORMATION: OLIGONUCLEOTIDE PRIMER PB880; CORRESPONDING TO
      SEQ ID NO:5 AT 2061-2076

<400> SEQUENCE: 14
atggatcagc aatgag                                                       16

<210> SEQ ID NO 15
<211> LENGTH: 26

```
<212> TYPE: DNA
<213> ORGANISM: Artificial
<220> FEATURE:
<223> OTHER INFORMATION: OLIGONUCLEOTIDE PRIMER PB2931

<400> SEQUENCE: 15
ctgtcaagcc aataaaaggg ttgttt                                    26

<210> SEQ ID NO 16
<211> LENGTH: 26
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 16
ctgtcaagcc aataaaaggg ttgttt                                    26

<210> SEQ ID NO 17
<211> LENGTH: 20
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 17
caactcgtcc gtgagcatca                                           20

<210> SEQ ID NO 18
<211> LENGTH: 24
<212> TYPE: DNA
<213> ORGANISM: Artificial
<220> FEATURE:
<223> OTHER INFORMATION: CONTIGUOUS NUCLEOTIDE AS SET FORTH IN REVERSE
      COMPLEMENT OF SEQUENCE CORRESPONDING TO SEQ ID NO:5 AT 4605-4628

<400> SEQUENCE: 18
aactcagcac tacggtgtat ccaa                                      24

<210> SEQ ID NO 19
<211> LENGTH: 16
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 19
gcctgccgca gaccaa                                               16

<210> SEQ ID NO 20
<211> LENGTH: 22
<212> TYPE: DNA
<213> ORGANISM: Artificial
<220> FEATURE:
<223> OTHER INFORMATION: CONTIGUOUS NUCLEOTIDE AS SET FORTH IN SEQ ID
      NO:5

<400> SEQUENCE: 20
caatgcagag ctcagcttca tc                                        22

<210> SEQ ID NO 21
<211> LENGTH: 17
<212> TYPE: DNA
<213> ORGANISM: Artificial
```

```
<220> FEATURE:
<223> OTHER INFORMATION: OLIGONUCLEOTIDE PRIMER PB351; CORRESPONDING TO
      SEQ ID NO:5 AT 4587-4603

<400> SEQUENCE: 21
cagagctcct atgttct                                                      17

<210> SEQ ID NO 22
<211> LENGTH: 26
<212> TYPE: DNA
<213> ORGANISM: Artificial
<220> FEATURE:
<223> OTHER INFORMATION: OLIGONUCLEOTIDE PRIMER SEQUENCE

<400> SEQUENCE: 22
tccagtacgt gcagtccctc ctccct                                            26
```

CORN PLANT AND SEED CORRESPONDING TO TRANSGENIC EVENT MON89034 AND METHODS FOR DETECTION AND USE THEREOF

CROSS REFERENCE TO RELATED APPLICATIONS

This application is a divisional of U.S. patent application Ser. No. 13/114,022, filed May 23, 2011, now U.S. Pat. No. 8,581,047, which application is a continuation of U.S. patent application Ser. No. 11/753,574, filed May 25, 2007, now issued as U.S. Pat. No. 8,062,840, which claims the benefit of U.S. Provisional Application Ser. No. 60/808,834, filed May 26, 2006, each of the disclosures of which are incorporated herein by reference in their entirety.

FIELD OF THE INVENTION

The present invention relates to transgenic corn event MON89034 and plant parts and seed thereof. The event exhibits resistance to insect infestation from insects in the order Lepidoptera. The invention also relates to methods for using plants and seeds comprising DNA that is diagnostic for the presence of the transgenic event when probed for the presence of nucleotide sequences that are unique to the transgenic event, and to methods for detecting the presence of said corn event in a biological sample by detecting specific nucleotide sequences that are unique to the transgenic event. The invention provides nucleotide sequences that are unique to the event.

BACKGROUND OF THE INVENTION

This invention relates to the Lepidopteran resistant transgenic variety of corn (Zea mays) plant referred to herein as event MON89034, and to unique DNA sequences present that, when detected in any sample or variety of corn, are diagnostic for the presence of the transgenic corn plant event MON89034 in that sample or variety, and also relates to the detection of the transgene/genomic insertion region in corn MON89034, and progeny plants and seeds derived therefrom.

The corn plant event MON89034 is particularly resistant to insects in the Lepidoptera family such as Fall armyworm (*Spodoptera frugiperda*), European corn borer (*Ostrinia nubilalis*), corn earworm (*Helicoverpa zea*), southwestern corn borer (*Diatraea Grandiosella*), and black cutworm (*Agrotis ipsilon*) and the like, all of which are agronomically important insect pests.

Corn is an important crop and is a primary food source in many areas of the world. Biotechnology methods have been applied to corn for the purpose of improving agronomic traits and the quality of the product. One such agronomic trait is insect resistance, for example, genetically engineered resistance to lepidopteran and coleopteran species that arises in corn plants genetically engineered to contain one or more genes encoding insecticidal agents (see for example, U.S. Pat. Nos. 6,489,542 and 6,620,988). It is advantageous to detect the presence of a particular transgenic event in a biological sample in order to determine whether one or more progeny of a sexual cross contains the transgenic material. For example, the detection of the event in a sample is important for licensing purposes, for establishing and maintaining purity standards, important for complying with regulatory agencies, for complying with food ingredient standards, for use in legal proceedings in establishing that one or more particular individuals or entities has been using the particular event without a license from the owner or licensee of any patents directed to the transgenic event, and for insuring compliance with various government regulations and/or laws.

In addition, methods that enable the detection of a particular plant would be helpful when complying with regulations requiring the pre-market approval and labeling of foods derived from the recombinant crop plants. Individuals or entities that are resistant to the presence of a transgenic event in a sample also desire reliable methods for detecting the presence of the transgene in a sample in order for them to be able to capitalize on their business, which takes advantage of an absence of transgenes in their products.

Despite these advantages, it is possible that insects may evolve resistance to plants expressing only one *B. thuringiensis* δ-endotoxin. Such resistance, should it become widespread, would clearly limit the commercial value of germplasm containing single Bt genes.

One possible way of increasing the effectiveness of insecticidal agents provided via transgenic plants and directed at controlling target insect pests and contemporaneously reducing the likelihood of emergence of insect pests resistant to such insecticidal agents would be to ensure that transgenic crops express high levels of these insecticidal agents, such as *Bacillus thuringiensis* delta-endotoxins (McGaughey and Whalon (1992), Science 258:1451-55; Roush (1994) Biocontrol. Sci. Technol. 4:501-516). In addition, having a repository of insecticidal genes that are effective against groups of insect pests and which manifest their effects through different modes of action can safeguard against development of resistance. The onset of resistance could be substantially delayed as a result of providing a crop that expresses two or more insecticidal activities exhibiting overlapping toxicity to the same insect species. One means for achieving such dual modes of action could be to provide a plant expressing a Bt gene toxic to a particular insect species along with a dsRNA that is provided for the purpose of targeting for suppression an essential gene of the same insect species targeted by the Bt toxin, the dsRNA eliciting an RNAi response upon ingestion by the target pest, providing a means for redundancy in the event that the insect develops resistance either to the dsRNA or to the Bt gene. Alternatively, co-expression in a plant of two or more insecticidal toxins both toxic to the same insect species but each exhibiting a different mode of effectuating its killing activity, particularly when both are expressed at high levels, provides a means for effective resistance management. Examples of such insecticides useful in such combinations include but are not limited to Bt toxins, Xenorhabdus sp. or Photorhabdus sp. insecticidal proteins, deallergenized and de-glycosylated patatin proteins and/or permuteins, plant lectins, and the like.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al. (19880 Ann. Rev. Genet 22:421-477). For this reason, it is often necessary to screen a large number of events in order to identify an event characterized by optimal expression of an introduced gene of interest. Even then, with dozens or even hundreds of different transgenic events in hand, there is no certainty of success in identifying a single transgenic event that provides the optimum levels of expression of the at least two different toxins or insecticidal agents and lacks any undesirable agronomic deficiencies or phytotoxic effects, either as a result of the insertion into some essential or partially essential region of the plant genome, or as a result of toxic effects brought about by the levels of expression of the transgenes. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce several hundreds to several thousands different events and screen the events for a single event that has the desired transgene expression levels and patterns for commercial purposes. An event that has the desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are suitably adapted to specific local growing conditions.

It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, or even the coding sequence encoding the protein or dsRNA of interest expressed from the transgene(s), etc. As a result, such methods may not be useful for discriminating between different events, particularly those produced using the same DNA construct, unless the sequence of chromosomal DNA adjacent to the inserted DNA ("flanking DNA") is known. Depending on the method used for introducing the transgene (s) into a plant genome, abberant or unusual effects can be observed, which often severly complicate the identification of the plant genome sequences flanking the transgenic DNA that was intended to be introduced into the plant. Often, rearrangements of the inserted DNA, rearrangements of the flanking genome DNA, or rearrangements of both the inserted DNA and the flanking genome DNA are prevalent, and complicate the analysis of the insertional event being evaluated. Therefore, it is advantageous to have a means for selecting, for identifying, and for insuring the purity and characteristics of a particular transgenic event in a sample, and the only way to accomplish this is to identify one or more unique sequences associated only with the desired transgenic event, and the presence of such sequences in a biological sample containing DNA of the plant species into which the transgenic DNA was inserted to give rise to the event are thus diagnostic for the event in such sample.

SUMMARY OF THE INVENTION

The present invention is related to the transgenic corn plant designated MON89034 and progeny that are indistinguishable from corn event MON89034 (to the extent that they also contain at least one allele that corresponds to the inserted transgenic DNA) thereof having seed deposited on Mar. 28, 2006 with American Type Culture Collection (ATCC) with Accession No.PTA-7455. Another aspect of the invention is the progeny plants, or seeds, or regenerable parts of the plants and seeds of the corn event MON89034 that contain a polynucleotide selected from the group consisting of SEQ ID NO:1, SEQ ID NO:2, SEQ ID NO:3, SEQ ID NO:4, and SEQ ID NO:5. The invention also includes plant parts of the corn event MON89034 that include, but are not limited to pollen, ovule, flowers, shoots, roots, stalks, silks, tassels, ears, and leaves, so long as these parts contain at least the polynucleotides as set forth above. Novel genetic compositions contained in the genome of MON89034 and products such from MON89034 such as meal, flour, oil, pulp, and biomass left over in a field of corn plants corresponding to MON89034 event are an aspect of this invention.

The invention provides an insect resistant corn plant that has all of the physiological and morphological characteristics of the corn event MON89034.

According to one aspect of the invention, compositions and methods are provided for detecting the presence of the transgene/genomic insertion region from a novel corn plant designated MON89034. DNA sequences are provided that comprise at least one junction sequence of MON89034 selected from the group consisting of SEQ ID NO:1 (located at positions 2051 to 2070 on SEQ ID NO: 5) and SEQ ID NO:2 (located at positions 11367 to 11388) and complements thereof; wherein a junction sequence spans the junction between heterologous DNA inserted into the genome and the DNA from the corn cell flanking the insertion site and is diagnostic for the event (FIG. 1). A corn event MON89034 and seed comprising these DNA molecules is an aspect of this invention.

DNA sequences that comprise the novel transgene/genomic insertion region, SEQ ID NO:3 and SEQ ID NO:4 (FIG. 2) from corn event MON89034 are aspects of this invention. The corn plant and seed comprising these molecules are also aspects of this invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:3 and a DNA molecule of similar length of any portion of a 5' flanking corn genomic DNA region of SEQ ID NO:3, where these DNA molecules when used together are useful as DNA primers in a DNA amplification method that produces an amplicon. The amplicon produced using these DNA primers in the DNA amplification method is diagnostic for corn event MON 89304 when the amplicon contains SEQ ID NO:1. Any amplicon produced by DNA primers homologous or complementary to any portion of SEQ ID NO:3 and any amplicon that comprises SEQ ID NO:1 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:4 and a DNA molecule of similar length of any portion of a 3' flanking corn genomic DNA of SEQ ID NO:4, where these DNA molecules are useful as DNA primers in a DNA amplification method. The amplicon produced using these DNA primers in the DNA amplification method is diagnostic for corn event MON 89304 when the amplicon contains SEQ ID NO:2. Any amplicons produced by DNA primers homologous or complementary to any portion of SEQ ID NO:4 and any amplicon that comprises SEQ ID NO:2 is an aspect of the invention.

According to another aspect of the invention, methods of detecting the presence of DNA corresponding to the corn event MON89034 in a sample are provided. Such methods comprise: (a) contacting the sample comprising DNA with a primer set that, when used in a nucleic acid amplification reaction with genomic DNA from corn event MON89034, produces an amplicon that is diagnostic for corn event MON89034; (b) performing a nucleic acid amplification reaction, thereby producing the amplicon; and (c) detecting the amplicon wherein said amplicon comprises SEQ ID NO:1 or SEQ ID NO:2.

A corn plant, or seed, or product derived from the plant or seed MON89034 wherein the genomic DNA comprising comprises a DNA molecule consisting essentially of SEQ ID NO:5 and complements thereof. A corn plant, or seed, or product derived from the plant or seed MON89034, in which the genomic DNA when isolated from the corn plant, or seed, or product comprises a DNA molecule incorporating nucleotides 2061 to 11377 of SEQ ID NO:5 and complements thereof.

A corn plant, or seed, or product derived from the plant or seed MON89034, in which the genomic DNA when isolated from the corn plant, or seed, or product produces an amplicon in a DNA amplification method, wherein DNA primer molecules SEQ ID NO:6 and SEQ ID NO:7 is used in the DNA amplification method.

According to another aspect of the invention, methods of detecting the presence of a DNA corresponding to the MON89034 event in a sample, such methods comprising: (a) contacting the sample comprising DNA with a probe that hybridizes under stringent hybridization conditions with genomic DNA from corn event MON89034 and does not hybridize under the stringent hybridization conditions with a control corn plant; (b) subjecting the sample and probe to stringent hybridization conditions; and (c) detecting hybridization of the probe to the corn event MON89034 DNA wherein said probe comprises SEQ ID NO:1 and SEQ ID NO:2.

Another aspect of the invention is a method of determining the zygosity of the progeny of corn event MON89034 comprising: (a) contacting the sample comprising corn DNA with a primer set comprising SQ2842 (SEQ ID NO:6), SQ2843(SEQ ID NO:7), SQ6523(SEQ ID NO:10), SQ6524 (SEQ ID NO:11), PB880 (SEQ ID NO:14) and PB2931 (SEQ ID NO:15) that when used in a nucleic-acid amplification reaction with genomic DNA from corn event MON89034, produces a first amplicon that is diagnostic for corn event MON89034 and (b) performing a nucleic acid amplification reaction, thereby producing the first amplicon; and (c) detecting the first amplicon; and (d) contacting the sample comprising corn DNA with said primer set, that when used in a nucleic-acid amplification reaction with genomic DNA from corn plants produces a second amplicon comprising the native corn genomic DNA homologous to the corn genomic region of a transgene insertion identified as corn event MON89034; and (e) performing a nucleic acid amplification reaction, thereby producing the second amplicon and (f) detecting the second amplicon; and (g) comparing the first and second amplicons in a sample, wherein the presence of both amplicons indicates the sample is heterozygous for the transgene insertion.

One aspect of the invention is providing in the diet of a lepidopteran pest an insecticidally effective amount of corn event MON89034.

Another aspect of the present invention is providing a composition or biological sample in the form of a commodity or foodstuff that is derived from corn event MON89034, the commodity or foodstuff comprising ears of corn, shucked corn, corn silk, corn pollen, cracked corn, corn meal, crushed corn, corn flour, corn oil, corn starch, corn steep liquor, corn malt, corn sugar, corn syrup, margarine produced from corn oil, unsaturated corn oil, saturated corn oil, corn flakes, pop corn, ethanol and/or liquor produced from corn or corn products comprising DNA diagnostic for corn event MON89034, distillers dry goods solids (DDGS) produced from fermentation of such corn event, and animal feeds comprising such DDGS and/or corn, whether or not whole, cracked, or crushed, processed foodstuffs, a cosmetic, and a bulking agent in which there is found a detectable amount of a polynucleotide that is diagnostic for the presence of the transgenic corn event MON89034 in the biological sample. An alternative means for providing corn as a foodstuff is to provide corn in various forms of grain for feeding, such as whole corn, cracked corn, crushed corn, and various forms of the foregoing in a blend with milo, suet, millet, sunflower, oats, wheat, rice, beans, and the like. Detectable amounts of a nucleotide sequence in such commodity or foodstuff, such as is set forth at SEQ ID NO:1 or SEQ ID NO:2, or the complements thereof, is diagnostic for the presence of such transgenic event MON89034 DNA in the sample, and therefore, the presence of the transgenic event cells as having originated the DNA in the sample.

The foregoing and other aspects of the invention will become more apparent from the following detailed description.

DRAWINGS

FIG. 1. Organization of the transgene insert present within the genome of transgenic corn event MON89034. The central open or white bar represents the inserted DNA. Below the white bar is a diagram that represents the various elements within the inserted DNA. The ends of the inserted DNA have been arbitrarily designated as 5' (to the left side of the Figure) and 3' (to the right side of the Figure). The Right Border and Left Border sequences or segments are labeled beneath each end of the diagram illustrating the various elements within the inserted DNA. The labeled elements in the expression cassettes within the inserted DNA are, in consecutive order starting from the Right Border: e35S promoter, wheat CAB untranslated leader, rice actin intron, coding sequence for Cry1A.105, wheat HSP17 3' termination and polyadenylation sequence, FMV promoter, hsp70 intron, rubisco small subunit chloroplast targeting peptide coding sequence, Cry2Ab coding sequence, nos 3' termination and polyadenylation signal sequence, and then the Left Border. The vertically hatched bars at either end of the central open or white bar correspond to the arbitrarily labeled 5' and 3' corn genome flanking sequences. The longest black line above the hatched and open or white bar represents SEQ ID NO:5 (the full length sequence represented by the figure depicting the 5' flanking sequence, the inserted DNA sequence, and the 3' flanking sequence). The shorter black lines above and below the black line labeled as SEQ ID NO:5 represent the approximate positions within SEQ ID NO:5 in which each of the specifically labeled sequences can be found (i.e., SEQ ID NO:1, SEQ ID NO:2, SEQ ID NO:3, and SEQ ID NO:4). SEQ ID NO:1 and SEQ ID NO:2, and any sequence derived from corn event MON89034 containing SEQ ID NO:1 and/or SEQ ID NO:2, are diagnostic for corn event MON89034 DNA in a biological sample.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994.

As used herein, the term "corn" means *Zea mays* or maize and includes all plant varieties that can be bred with corn, including wild maize species.

As used herein, the term "comprising" means "including but not limited to".

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The present invention relates to the event MON89034 DNA, plant cells, tissues, seeds and processed products derived from MON89034.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from corn event MON89034 whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: Nucleic Acid Hybridization, A Practical Approach, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO: 1 and 2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 and SEQ ID NO:2 or complements or fragments of either under high stringency conditions. In one aspect of the present invention, a preferred marker nucleic acid molecule of the present invention has the nucleic acid sequence set forth in SEQ ID NO:1 and SEQ ID NO:2 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:1 and SEQ ID NO:2 or complement thereof or fragments of either. In a further aspect of the present invention, a preferred marker nucleic acid molecule of the present invention shares between 95% and 100% sequence identity with the sequence set forth in SEQ ID NO:1 and SEQ ID NO:2 or complement thereof or fragments of either. SEQ ID NO:1 and SEQ ID NO:2 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the corn plant resulting from a sexual cross contains transgenic event genomic DNA from the corn plant of the present invention, DNA extracted from a corn plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from corn event MON89034 with seed samples deposited as ATCC numbers can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTP's are added individually and the incorporation results in a light signal which is measured. A light signal indicates the presence of the transgene insert/flanking sequence due to successful amplification, hybridization, and single or multi-base extension.

Fluorescence polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorimeter. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the flanking/transgene insert sequence due to successful amplification and hybridization.

Other described methods, such as, microfluidics (US Patent pub. 2006068398, U.S. Pat. No. 6,544,734) provide methods and devices to separate and amplify DNA samples. Optical dyes used to detect and quantitate specific DNA molecules (WO/05017181). Nanotube devices (WO/06024023) that comprise an electronic sensor for the detection of DNA molecules or nanobeads that bind specific DNA molecules and can then be detected.

DNA detection kits are provided using the compositions disclosed herein. The kits are useful for the identification of corn event MON89034 DNA in a sample and can be applied at least to methods for breeding corn plants containing the appropriate event DNA. The kits contain DNA primers and/or probes that are homologous or complementary to segments selected from the sequences as set forth at SEQ ID NO:1-7, or DNA primers or probes homologous or complementary to DNA contained in the transgene genetic elements of DNA as set forth in the Sequence Listing. These DNA sequences can be used in DNA amplification reactions or as probes in a DNA hybridization method for detecting the presence of polynucleotides diagnostic for the presence of the target DNA in a sample. The production of a predefined amplicon in a thermal amplification reaction is diagnostic for the presence of DNA corresponding to PTO-7455 genome DNA in the sample. If hybridization is selected, detecting hybridization of the probe to the biological sample is diagnostic for the presence of the MON89034 transgenic event DNA in the sample. Typically, the sample is corn, or corn products or by-products of the use of corn.

The present invention provides a transgenic corn plant designated as corn event MON89034, progeny of the plant, and cells of the plant, as well as seed produced from the plant. Representative seed for growing the plant, for producing progeny, for obtaining cells, or for producing a crop of said seed comprising the transgenic corn event have been deposited on Mar. 28, 2006 with the American Type Culture Collection (ATCC) and have the accession number PTA-7455.

The plant and cells and products produced from these embodiments and the like contain DNA that is diagnostic for the presence of DNA derived from any cell derived from the transgenic corn event MON89034 in any biological sample. This is because these two novel sequences are contained within the cells of the transgenic corn event MON89034. The diagnostic DNA comprises a nucleotide sequence that is selected from the group consisting of SEQ ID NO:1, SEQ ID NO:2, SEQ ID NO:3, SEQ ID NO:4, and SEQ ID NO:5. The relationship of these sequences is described more particularly herein and in the legend to FIG. 1 and with reference to FIG. 1.

Corn plants grown from seed that are homozygous for the DNA diagnostic for transgenic corn event MON89034 are also within the scope of the present invention. Corn plants grown from seed that are heterozygous for the DNA diagnostic for transgenic corn event MON89034 are also within the scope of the present invention so long as these seed also comprise the diagnostic DNA sequences. Cells, seed, and tissue produced from such plants comprising the diagnostic DNA are also within the scope of the present invention.

Corn plants, corn plant cells, pollen, ova, and the like comprising DNA diagnostic for the transgenic corn event MON89034 exhibit resistance to lepidopteran insect infestation. These cells and plants contain DNA encoding the insecticidal protein (insecticide, toxic agent) Cry2Ab and DNA having nucleotide sequences of SEQ ID NO:1 and SEQ ID NO:2 that form a part of the genome of the cells of the plant. These plants and plant cells also contain a DNA encoding insecticidal protein (insecticide, toxic agent) Cry1A.105. These proteins can be referred to as a first and a second insecticidal protein, respectively or in the inverse. Expression of these proteins is achieved from the regulatory components/genetic elements that are embedded within the expression cassettes that provide for the expression of each of the DNA sequences encoding these toxins and are fully described herein and in the legend to FIG. 1 and with reference to FIG. 1 and the sequence as set forth at SEQ ID NO:5. Corn plants and corn plant cells comprising these sequences are effective for protecting plants from lepidopteran pest infestation, whether heterozygous or homozygous for the alleles in which these coding sequences are present.

The present invention also provides amplicons that can be produced from the sequences described herein that are diagnostic for the presence in a biological sample of DNA derived from DNA of the transgenic corn event MON89034. An amplicon diagnostic for the presence of transgenic corn event MON89034 DNA in a biological sample contains at least one polynucleotide segment consisting of the nucleotide sequence as set forth at SEQ ID NO:1 or SEQ ID NO:2. These amplicons can be produced using primer sequences as described herein below from any biological sample that contains at least about 0.5 femto-mole or about 0.5 picogram of DNA derived from the transgenic corn event MON89034.

Such biological sample sources of DNA corresponding to the transgenic corn event MON89034 can be corn meal, corn oil, corn cake, corn seed, corn germ, corn starch, and corn flour and the like derived form that transgenic event.

The invention also provides isolated polynucleotide molecules that exhibit contiguous nucleotide sequences such as those set forth in SEQ ID NO:5. These contiguous nucleotide sequences comprise: (1) from about 11 to about 12000 nucleotides and any length in-between, and further comprise the contiguous nucleotides as set forth at nucleotide position 1-11 or 9-20 in SEQ ID NO:1 and 1-11 or 9-20 as set forth in SEQ ID NO:2; (2) any contiguous nucleotide sequence as set forth in SEQ ID NO:3 from about 11 to about 2000 nucleotides and any length in-between, and further comprise the contiguous nucleotides as set forth at nucleotide position 1-11 and 9-20 as set forth at SEQ ID NO:1; any contiguous nucleotide sequence as set forth in SEQ ID NO:4 from about 11 to about 914 nucleotides and any length in-between, and further comprise the contiguous nucleotides as set forth at nucleotide position 1-11 and 9-20 as set forth at SEQ ID NO:2. These isolated polynucleotide molecules are useful in DNA amplification methods to produce one or more amplicons from a biological sample that contains corn DNA. The detection of such an amplicon is diagnostic for the presence of transgenic corn event MON89034 DNA in the sample. The isolated polynucleotide molecules are also useful in various nucleotide detection methods for detecting the presence of DNA derived from transgenic corn event MON89034 in a biological sample. In particular, polynucleotide probes comprising at least about 11 contiguous nucleotide as set forth in SEQ ID NO:1 or SEQ ID NO:2 are useful as probes in such methods for detecting the transgenic event MON89034 DNA in a sample. The complementary sequences of these isolated polynucleotide molecules are also useful in the same detection and/or amplification methods.

Kits for use in detecting the presence of DNA derived from the transgenic corn event MON89034 in a biological sample are also provide by the present invention. A kit uses a probe polynucleotide molecule, the probe molecule containing at least from about 11 to about 12000 contiguous nucleotides exhibiting substantial homology, or exhibiting substantial complementarity to a nucleotide segment comprising a sequence as set forth at SEQ ID NO:5, would be useful for detecting the presence of MON89034 DNA in a sample. The probe molecule should contain at least one of the sequences as set forth at SEQ ID NO:1 and SEQ ID NO:2, or the complements thereof. The sequences set forth at SEQ ID NO:1 and SEQ ID NO:2 are also referred to as junction sequences, i.e., the sequences within the MON89034 transgenic event genome corresponding to the contiguous sequences at which the interrupted native genome sequence and the transgenic DNA sequence inserted into the corn plant meet, are connected, or are joined together. These junction sequences, arbitrarily referred to as 5' and 3' ends respectively, i.e., SEQ ID NO:1 and SEQ ID NO:2 respectively, and the complements thereof, each contain part of the inserted DNA sequence and part of the flanking corn genome sequence. For example, SEQ ID NO:1 represents at its 5' half the 3' end terminus of the corn genome sequence flanking the 5' end of the inserted DNA, the 5' end of the inserted DNA being represented by the 3' end half of the sequence as set forth at SEQ ID NO:1. SEQ ID NO:2 represents at its 5' half the 3' end terminus of the inserted DNA, and at its 3' end half the 5' end of the corn genome sequence flanking the 3' end of the inserted DNA. In the naturally occurring corn genome at the position of the inserted sequence set forth in SEQ ID NO:5, the flanking sequence at the 5' end of the inserted DNA and the flanking sequence at the 3' end of the inserted DNA are joined, and a first primer molecule that hybridizes to the sequence complementary to the sequence set forth at SEQ ID NO:3 (other than the 3' end 21 nucleotides of SEQ ID NO:3) and a second primer molecule that hybridizes to the sequence as set forth at SEQ ID NO:4 (other than the 5' end 20 nucleotides of SEQ ID NO:4) will produce an amplicon in a thermal amplification reaction with template that is DNA other than MON89034 DNA that is diagnostic for the absence of the inserted DNA in MON89034, and the same primers will produce an amplicon that is slightly larger than 12000 nucleotides (depending on the position of the primers in the flanking sequences set forth in SEQ ID NO:3 and SEQ ID NO:4) when using MON89034 DNA as a template. Other embodiments are also provided.

A kit for detecting the junction sequence SEQ ID NO:1 or SEQ ID NO:2 of corn event MON89034 in a biological sample is provided. The kit contains a polynucleotide probe which is or is fully complementary to a sequence selected from the group consisting of SEQ ID NO:1 or SEQ ID NO:2 or complements thereof, and also contains a pair of primers for use in a nucleic-acid amplification reaction. The pair of primers can be referred to as a first primer consisting of at least about 15 to about 50 contiguous nucleotides from the corn genome portion of SEQ ID NO:3 and a second primer consisting of at least about 15 to about 50 contiguous nucleotides complementary to the heterologous insert DNA portion of SEQ ID NO:5. The first primer of the pair of polynucleotide primers hybridizes specifically to the reverse complement sequence corresponding to that set forth in SEQ ID NO:3 from about nucleotide position 1 through about position 2050 and the second primer of said pair of polynucleotide primers hybridizes specifically to the sequence as set forth in SEQ ID NO:5 from about nucleotide position 2060 through about nucleotide position 12,208, and are extended toward each other to form an amplicon which comprises SEQ ID NO:1, said amplicon being diagnostic for the presence of MON89034 event DNA in the sample. A different pair of primers can be referred to as a first primer consisting of at least about 15 to about 50 contiguous nucleotides complementary to the corn genome portion of SEQ ID NO:4 and a second primer consisting of at least about 15 to about 50 contiguous nucleotides from the heterologous insert DNA portion of SEQ ID NO:5. The first primer of the pair of polynucleotide primers hybridizes specifically to the reverse complement sequence corresponding to that set forth in SEQ ID NO:5 from about nucleotide position 1 through about position 11,370 and the second primer of the pair of polynucleotide primers hybridizes specifically to the sequence as set forth SEQ ID NO:4 from about nucleotide position 1 through about nucleotide position 914, and are extended toward each other to form an amplicon which comprises SEQ ID NO:2, said amplicon being diagnostic for the presence of MON89034 event DNA in said sample.

These primer pairs are useful in producing amplicons that comprise either SEQ ID NO:1 or SEQ ID NO:2, as the case may be, and are thus diagnostic for the presence of MON89034 DNA in a biological sample. These amplicons enable the detection of the presence of a junction sequence diagnostic corn event MON89034 in a biological sample.

A method for producing and detecting an amplicon that is diagnostic for a transgenic corn event MON89034 DNA in a biological sample comprising corn DNA is also provided. The method comprises contacting the biological sample together with two or more primers in a nucleic acid amplification reaction, performing a nucleic acid amplification reaction, then detecting the amplicon. The presence of the amplicon is diagnostic for said event DNA in the sample so long as the amplicon contains at least one of the contiguous sequences as set forth at SEQ ID NO:1 and SEQ ID NO:2, from about nucleotide position 1-11 or 9-20, or the complementary sequences corresponding to these positions.

The nucleotide sequences diagnostic for the presence of transgenic corn event MON89034 in a biological sample can also be detected using other methods. For example, contacting a biological sample suspected of containing MON89034 DNA with a probe that hybridizes under stringent hybridization conditions with one or more of the nucleotide sequences as set forth at SEQ ID NO:1 or SEQ ID NO:2, subjecting the sample and probe to stringent hybridization conditions; and then detecting hybridization of the probe to the nucleotide sequence. Detecting hybridization is diagnostic for the presence of the MON89034 DNA in the sample.

Primer polynucleotides for use in producing, in a thermal amplification reaction, an amplicon that is diagnostic for the presence of corn event MON89034 DNA in a biological sample are also provided by the present invention. Typically, the primers are provided in pairs, the members of the primer pair being referred to for convenience as a first primer and a second primer. A first primer can consist of at least about 15 contiguous nucleotides from the corn genome portion as set forth in SEQ ID NO:3 and a second primer can consist of at least about 15 contiguous nucleotides complementary to the heterologous insert DNA portion as set forth in SEQ ID NO:5. These two primers would produce an amplicon in a thermal amplification reaction with template DNA obtained from corn event MON89034 DNA that contains a polynucleotide sequence as set forth at SEQ ID NO:1. Alternatively, a first primer can consist of at least about 15 contiguous nucleotides from the corn genome portion of SEQ ID NO:4, and a second primer can consist of at least about 15 contiguous nucleotides complementary to the heterologous insert DNA portion of SEQ ID NO:5. These two primers would produce an amplicon in a thermal amplification reaction with template DNA obtained from corn event MON89034 DNA that contains a polynucleotide sequence as set forth at SEQ ID NO:2.

An alternative method for detecting a junction sequence of corn event MON89034 in a biological sample comprising corn DNA, such as SEQ ID NO:1 or SEQ ID NO:2, consists of contacting the sample with a polynucleotide probe that hybridizes under stringent hybridization conditions with one of the junction sequences, subjecting the sample and probe to stringent hybridization conditions; and detecting hybridization of the probe to the junction sequence. Detecting the binding/hybridization of the probe to the junction sequence is indicative of the presence of the MON89034 DNA in the biological sample. A stably transformed maize plant, the DNA of which produces a DNA amplicon comprising SEQ ID NO:1 or SEQ ID NO:2 when subjected to the method set forth herein, is within the scope of the present invention. Exemplary primer sequences, in particular, a pair of primer sequences, are set forth herein in the examples and at SEQ ID NO:6 and SEQ ID NO:7.

An alternative method of detecting the presence of corn event MON89034 DNA in a biological sample can consist of the steps of contacting the sample with a probe that hybridizes under stringent hybridization conditions with MON89034 DNA and does not hybridize under stringent hybridization conditions with corn plant genomic DNA that is not MON89034 DNA, subjecting the sample and probe to stringent hybridization conditions, and then detecting hybridization of the probe to MON89034 DNA. A probe consistent with this embodiment is or is complementary to a sequence selected from the group consisting of SEQ ID NO:1 and SEQ ID NO:2. Detecting hybridization of the probe to the sample is diagnostic for the presence of the corn event MON89034 polynucleotide in the sample. The biological sample can be any sample containing MON89034 DNA including but not limited to corn oil, corn meal, corn flour, corn gluten, corn cakes, corn starch, corn steep liquor, corn tissue, corn cells, corn grain, corn pollen, corn root tissue, DDGS, and even ethanol produced as a byproduct of fermentation of such transgenic corn so long as the sample contains at least a detectable amount of a polynucleotide diagnostic for the presence of the MON89034 event in the sample. A polynucleotide probe can be any nucleotide selected from the group consisting of a deoxyribonucleic acid, a ribonucleic acid, and a nucleotide analogue, and can be labeled with at least one fluorophores, molecule containing a radio-emitting isotope, or a hapten type molecule that can be detected specifically with an antibody or other binding type reaction.

A variety of corn comprising a DNA diagnostic for the presence of a MON89034 transgenic event DNA can be obtained by breeding a corn plant comprising transgenic corn event MON89034 DNA together with a corn plant other than event MON89034 to produce a hybrid corn plant comprising DNA diagnostic for said event. Such a hybrid corn plant comprising DNA diagnostic for the transgenic corn event MON89034 is within the scope of the present invention, as are seed produced from the hybrid (so long as the comprises DNA diagnostic for transgenic corn event MON89034), and pollen, ovule, seed, roots, or leaves of the hybrid corn plant MON89034, also to the extent these contain the diagnostic DNA sequences, and progeny produced from such embodiments.

The present invention provides a method for protecting a corn plant from lepidopteran insect infestation comprising providing in the diet of a target lepidopteran insect pest one or more transgenic corn plant cells, each corn plant cell comprising in its genome a polynucleotide corresponding to the sequence as set forth in both SEQ ID NO:1 and SEQ ID NO:2 and the contiguous nucleotide sequence as set forth in SEQ ID NO:5 between SEQ ID NO:1 and SEQ ID NO:2. The target lepidopteran insect that feeds on such transgenic corn plant cells is inhibited from further feeding on the corn plant from which the corn plant cells are derived.

Compositions are also provided by the present invention that are toxic to target lepidopteran pests of corn plants. A composition of transgenic plant cells provided in the diet of a target lepidopteran insect pest, in which each transgenic corn plant cell comprises in its genome a polynucleotide corresponding to the sequence as set forth in both SEQ ID NO:1 and SEQ ID NO:2, along with the contiguous nucleotide sequence as set forth in SEQ ID NO:5 between SEQ ID NO:1 and SEQ ID NO:2, is effective for providing protection against lepidopteran insect infestation to a corn plant or corn plant cell, so long as the corn plant or cell is expressing Cry1A.105 and/or Cry2Ab2 from the expression cassettes contained within the contiguous nucleotide sequence. Such compositions, in the form of transgenic corn seed, have been deposited with the American Type Culture Collection under accession number PTA-7455. Such insect resistant corn plants, or parts thereof, will contain DNA in the genome of the cells of such plant that have at least one nucleotide sequence selected from the group consisting of SEQ ID NO:1, SEQ ID NO:2, SEQ ID NO:3, SEQ ID NO:4, and SEQ ID NO:5. Progeny and seed of the insect resistant corn plant, in which the progeny and seed have the diagnostic sequences referred to herein, are also included within the scope of the present invention. Such insect resistant corn plants can be produced in a method comprising crossing a transgenic corn plant event MON89034 with a different corn plant, and selecting insect resistant progeny by analyzing for at least one nucleotide sequence selected from the group consisting of SEQ ID NO:1, SEQ ID NO:2, SEQ ID NO:3, SEQ ID NO:4 and SEQ ID NO:5.

The insect resistant transgenic corn event MON89034 can be combined with other transgenic varieties of corn, such as corn resistant to herbicides such as glyphosate, glufosinate, and diacamba, and the like, or corn resistant to root devouring insects as a result of insertion of sequences encoding proteins such as PS 149B1 and modified Cry3Bb, or other varieties of transgenic corn resistant to lepidopteran insect infestation as a result of insertion of sequences encoding other toxin proteins such as VIP3A, Cry1Ab, and Cry1Fa and the like. Various combinations of all of these different transgenic events are bred together with the corn plants of the present invention, i.e., the MON89034 event, to provide improved varieties of hybrid transgenic corn resistant to coleopteran and lepidopteran infestation, and resistant to selective herbicides. Such varieties exhibit improved yield and drought tolerance characteristics compared to non-transgenic and individual trait transgenic varieties.

A method of producing a corn plant resistant to insect infestation is provided, wherein the corn plant comprises an insecticidally effective amount of the toxin coding sequences as set forth in SEQ ID NO:5. The method comprises extracting the toxin coding sequences from transgenic corn event MON89034 and introducing these coding sequences, alone or together, into one or more corn cells, to produce transgenic corn cells comprising these one or more toxin coding sequences. The transgenic corn cells are then grown (regenerated) into transgenic corn plants comprising the one or more coding sequences, and the transgenic plants then exhibit resistance to insect infestation.

A method for determining the zygosity of the DNA of a transgenic corn plant comprising corn event MON89034 DNA, with respect to the DNA that is diagnostic for the presence of such MON89034 DNA in a biological sample, is provided by the present invention. The method consists of, as a first step, contacting the sample with three different primers comprising SEQ ID NO:6, SEQ ID NO:7, and SEQ ID NO:10, that when used together in a nucleic-acid amplification reaction comprising corn event MON89034 DNA, produces a first amplicon that is diagnostic for corn event MON89034, and when used in a nucleic-acid amplification reaction comprising corn genomic DNA other than MON89034 DNA, produces a second amplicon that is diagnostic for corn genomic DNA other than MON89034 DNA. The following steps consist of performing a nucleic acid amplification reaction, and comparing the amplicons produced during the thermal amplification reaction. Detecting the presence of both amplicons is diagnostic of the zygosity of the sample. Detecting only the first amplicon is indicative of the sample containing only MON89034 DNA, i.e., a homozygous sample. Detecting only the second amplicon is indicative of the sample containing no MON89034 DNA. Detecting both the first and second amplicons together in a sample is indicative of a sample containing (1) heterozygous DNA with reference to a pure sample containing only heterozygous starting material, or (2) a sample containing both homozygous and heterozygous starting sample DNA's, or (3) a sample containing some combination of homozygous, heterozygous, and/or samples other than MON89034 DNA.

The invention also provides for growing corn plants comprising DNA diagnostic for a transgenic DNA segment inserted into the genome of the cells of the corn plants. The DNA in the genome of the corn cells comprises any one or all of the sequences selected from the group consisting of:
(a) the nucleotide sequence as set forth in SEQ ID NO:5;
(b) both of the nucleotide sequences as set forth SEQ ID NO:1 and SEQ ID NO:2;
(c) the nucleotide sequence as set forth at SEQ ID NO:3; and
(d) the nucleotide sequence as set forth at SEQ ID NO:4.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

This Example illustrates the construction and molecular characterization of transgenic corn event MON89034.

The corn plant MON89034 was produced by an Agrobacterium mediated transformation process of an inbred corn line with the plasmid construct pMON38850 (the expression cassette is shown in FIG. 1). The transformation method used is similar to that described in U.S. Pat. No. 6,603,061. The plasmid construct pMON38850 contains the linked plant expression cassettes with the regulatory genetic elements necessary for expression of the Cry1A.105 insecticidal protein in corn plant cells. Corn cells were regenerated into intact corn plants consisting of at least about 23,000 different transgenic events. Individual transgenic events (plants) were selected from the population of events that showed integrity of the plant expression cassettes and resistance to Lepidopteran insect larvae feeding damage. A corn plant that contains in its genome the linked plant expression cassettes of pMON38850 is an aspect of the present invention. After substantial analysis of these transgenic events, the MON89034 transgenic event was selected on the basis of its molecular characterization and the absence of any undesirable phenotypic or agronomic deficiency effects.

The sequences of the transgene genetic elements contained in MON89034 corn genome as illustrated in FIG. 1 consists of the following elements each in operable linkage to each other. First at the arbitrarily defined 5' end of the sequence (i.e., near the left central portion of the segment depicted in FIG. 1) is labeled a portion of the right border region (RB) from Agrobacterium tumefaciens. This is followed in sequence by an expression cassette consisting of an enhanced CaMV 35S promoter element (herein referred to as P-CaMV35Sen, located at positions 2350 to 2651 on SEQ ID NO:5); a wheat chlorophyll A/B binding protein untranslated leader sequence (herein referred to as L-Ta.lhcb1, located at positions 2678 to 2738 on SEQ ID NO:5); a rice actin intron sequence (herein referred to as I-Os.Act1, located at positions 2755 to 3234 on SEQ ID NO:5); a non-naturally occurring sequence encoding the chimeric gene Cry1A.105 (located at positions 3244 to 6777 on SEQ ID NO:5); and a 3' termination region from wheat (herein referred to as T-Ta.Hsp17-1:1:1, located at positions 6809 to 7018 on SEQ ID NO:5). The combination of the above referenced elements, other than the border sequence, function together when in a corn plant to cause the expression of the Cry1A.105 insecticidal protein. These elements are then linked in sequence to another expression cassette consisting of the following elements: a Figwort mosaic promoter (located at positions 7086 to 7649 on SEQ ID NO:5), a *Zea mays* Hsp70 leader (herein referred to as HSP70 or I-Hsp70, located at positions 7672 to 8475 on SEQ ID NO:5), and a *Zea mays* chloroplast transit peptide coding sequence (herein referred to as CTP2 or TS-SSU-CTP, located at positions 8492 to 8892 on SEQ ID NO:5). These operably linked segments are then linked to a nucleotide sequence encoding the insecticidal protein Cry2Ab (located at positions 8893 to 10800 on SEQ ID NO:5), which is linked at its 3' end to a 3' non-translated region of the nopaline synthase gene of Agrobacterium tumefaciens (herein referred to as T-AGRtu.nos-1:1:13, located at positions 10827 to 11377 on SEQ ID NO:5). These elements flanking the Cry2Ab coding sequence function together to direct the expression of Cry2Ab when present in a corn plant. The Cry2Ab expression cassette is then followed in sequence by a nucleotide sequence consisting of a sufficient portion of the left border (LB) region from Agrobacterium tumefaciens.

DNA molecules useful as primers in DNA amplification methods can be derived from the sequences of the genetic elements of the transgene insert contained in the MON89034 event. These primer molecules can be used as part of a primer set that also includes a DNA primer molecule derived from the genome of event flanking the transgene insert.

The portion of the pMON38850 plasmid DNA inserted into the corn genome, giving rise to the transgenic corn plant event MON89034, consisting of the left and right border segments and the two linked plant expression cassettes (a first expression cassette encoding Cry1A.105, and a second expression cassette encoding Cry2Ab, wherein each cassette can be interchangeable as to whether one is designated as being a first or a second cassette) in between the border segments was characterized by detailed molecular analyses. These analyses were conducted to identify events that contained only a single and intact inserted segment consisting of the borders and the desired two expression cassettes in between the borders (number of integration sites within the corn genome), the copy number (the number of copies of the T-DNA within one locus), and the integrity of the inserted gene cassettes (i.e., absence of any rearrangements or sequence variation from the sequence known to be present in the plasmid pMON38850). DNA molecular probes were used that included the intact Cry1A.105 coding region and its respective regulatory elements, the promoters, introns, and polyadenylation sequences of the plant expression cassettes, and plasmid pMON38850 backbone DNA region. The data obtained from the analyses of all events demonstrated that MON89034 contains a single T-DNA insertion with one copy of the Cry1A.105 expression cassette. No additional elements from the transformation vector pMON38850, linked or unlinked to intact gene cassettes, were detected in the genome of MON89034. Finally, PCR and DNA sequence analyses were performed to determine the 5' and 3' insert-to-plant genome junctions, confirm the organization of the elements within the insert (see for example, FIG. 1), and determine the complete sequence of the DNA inserted into the corn plant genome that gave rise to the transgenic corn event MON89034. The complete inserted sequence, together with a portion of the corn genome flanking sequences at either end of the inserted DNA, is depicted in the sequence as set forth at SEQ ID NO:5.

Genomic DNA from MON89034, and non transgenic DNA from corn other than MON89034 (control DNA) was extracted from corn seed by first processing the seed (up to 200 seeds) to a fine powder in a Harbil 5G-HD paint shaker (Harbil Inc, Cincinnati, Ohio). Briefly, the powdered seed was extracted in extraction buffer (EM Science Cat. No. 3700, EM Science, Gibbstown, N.J., USA) and DNA precipitated from solution with isopropanol (Sigma Cat. No. I-0398, Sigma, St. Louis, Mo., USA). The precipitated DNA was spooled into a microcentrifuge tube containing 70 percent ethanol. The DNA was pelleted in a microcentrifuge at maximum speed (~14,000 rpm) for ~5 minutes, vacuum-dried, and re-dissolved in TE buffer (pH 8.0). The DNA was then stored in a 4° C. refrigerator. This method can be modified by one skilled in the art to extract DNA from a single corn seed.

Exemplary methods used to identify event MON89034 in a sample are described in an event specific endpoint Taqman PCR for which examples of conditions are described in Table 1 and Table 2. The DNA primers used in the assay are primers SQ2842 (SEQ ID NO:6), SQ2843 (SEQ ID NO:7), 6FAM™ labeled primer PB880 (SEQ ID NO:14) and VIC™ labeled primer PB2931 (SEQ ID NO:15), 6FAM and VIC are florescent dye products of Applied Biosystems (Foster City, Calif.) attached to the DNA primers. For Taqman MGB probes, the 5'-exonuclease activity of Taq DNA polymerase cleaves the probe from the 5'-end, between the fluorophore and quencher. When hybridized to the target DNA strand, quencher and fluorophore are separated sufficiently in three dimensional space to produce a fluorescent (fluorophore excitation wavelength) signal.

SQ2842 (SEQ ID NO:6), and SQ2843 (SEQ ID NO:7), when used in these reaction methods with PB880 (SEQ ID NO:14) produce a DNA amplicon that is diagnostic for event MON89034 DNA. The controls for this analysis should include a positive control from corn containing event MON89034 DNA, a negative control from non-transgenic corn or from transgenic corn other than event MON89034, and a negative control that contains no template DNA.

SQ1564 (SEQ ID NO:17) and SQ1565 (SEQ ID NO:18) when used in these reaction methods with PB351 (SEQ ID NO:21) produce an amplicon that is diagnostic of Cry1A.105 in MON89034.

purposes of the invention disclosed herein, to be diagnostic for the presence of the corn event MON89034 DNA in such biological sample. The following example is provided as reference for one skilled in the art.

TABLE 1

Corn MON89034 Event Specific Endpoint Taqman PCR

| Step | Reagent | Amount | Comments |
| --- | --- | --- | --- |
| 1 | Nuclease-free water | add to 10 µl final volume | — |
| 2 | 2X Universal Master Mix (Applied Biosystems cat. # 4304437) | 5 µl | 1 X final concentration |
| 3 | Primers SQ2842 (SEQ ID NO: 6), and SQ2843(SEQ ID NO: 7) resuspended in nuclease-free water to a concentration of 20 µM each) | 0.5 µl | 1.0 µM final concentration |
| 4 | Primer 6FAM ™ (resuspended in nuclease-free water to a concentration of 10 µM) | 0.2 µl | 0.2 µM final concentration |
| 5 | Internal Control Primer -SQ2842 and internal control primer SQ2843 | 0.2 µl | 0.2 µM final concentration |
| 6 | Extracted DNA (template): | 3.0 µl | Diluted in water |
|   | Samples to be analyzed (individual leaves) | 4-80 ng of genomic DNA | |
|   | Negative control | 4 ng of non-transgenic corn genomic DNA | |
|   | Negative control | no DNA template (solution in which DNA was resuspended) | |
|   | Positive control | 4 ng of genomic DNA from known event MON89034 heterozygous corn | |
|   | Positive control | 4 ng of genomic DNA from known event MON89034 homozygous corn | |
| 7 | Gently mix, add 1-2 drops of mineral oil on top of each reaction. | | |

These assays are optimized for use with an Applied Biosystems GeneAmp PCR System 9700 or Stratagene Robocycler, MJ Engine, Perkin-Elmer 9700, or Eppendorf Mastercycler Gradient thermocycler. Other methods and apparatus known to those skilled in the art that produce amplicons that identify the identify event MON89034 DNA is within the skill of the art.

Any probe that binds specifically to SEQ ID NO:1 or to its perfect complementary sequence in a biological sample and contains at least 11 contiguous nucleotides as set forth in SEQ ID NO:1, or as the case may be, the reverse complement of the sequence in SEQ ID NO:1, so long as the binding can be detected, is diagnostic for the presence of corn event MON89034 DNA in that sample. Any probe that binds specifically to SEQ ID NO:2 or to its perfect complementary sequence in a biological sample and contains at least 11 contiguous nucleotides as set forth in SEQ ID NO:2, or as the case may be, the reverse complement of the sequence in SEQ ID NO:2, so long as the binding can be detected, is diagnostic for the presence of corn event MON89034 DNA in that sample.

Any pair of primers that is used for or designed for use in producing an amplicon from a biological sample comprising corn DNA, and the amplicon comprises either SEQ ID NO:1 or SEQ ID NO:2, or as the case may be, comprises both sequences, is considered to be within the scope of the present invention. Any such amplicon comprising either SEQ ID NO:1 or SEQ ID NO:2 or both is considered, for the The DNA amplification can be set up and conducted using any means for thermocycling, including manual manipulations or electronically controlled manipulations of temperature steps and cycles. Stratagene Robocycler, MJ Engine, Perkin-Elmer 9700, or Eppendorf Mastercycler Gradient thermocycler or Applied Biosystems GeneAmp PCR System 9700 or MJ Research DNA Engine PTC-225 thermal cyclers have been used successfully to conduct the following cycling parameters. When running the PCR in the Eppendorf Mastercycler Gradient or MJ Engine, the thermocycler was cycled in the calculated mode. When using the Perkin-Elmer 9700, the cycling conditions were conducted with the ramp speed set at maximum.

TABLE 2

Zygosity assay thermocycler conditions

| Cycle No. | Settings: Applied Biosystems GeneAmp PCR System 9700 |
| --- | --- |
| 1 | 50° C. 2 minutes |
| 1 | 95° C. 10 minutes |
| 10 | 95° C. 15 seconds |
|   | 64° C. 1 minute (−1° C./cycle) |
| 30 | 95° C. 15 seconds |
|   | 54° C. 1 minute |
| 1 | 10° C. soak |

Example 2

This example illustrates the identification of a corn plant comprising DNA diagnostic for the transgenic corn event MON89034 in its genome and the determination of the zygosity of such corn plant.

The methods used to identify heterozygous from homozygous progeny containing event MON89034 DNA in its genome are described in a zygosity assay for which conditions are exemplified in Table 3 and Table 4. The exemplary DNA primers used in the zygosity assay are primers SQ2842 (SEQ ID NO: 6), SQ2843(SEQ ID NO:7), SQ6523(SEQ ID NO:10), SQ6524(SEQ ID NO:11), 6FAM™ labeled primer PB880(SEQ ID NO:14) and VIC™ labeled primer PB2931 (SEQ ID NO:15). As indicated above, 6FAM and VIC are florescent dye products of Applied Biosystems (Foster City, Calif.) attached to the DNA primer.

SQ2842 (SEQ ID NO:6), SQ2843(SEQ ID NO:7), SQ6523(SEQ ID NO:10), SQ6524(SEQ ID NO:11), when used together in a thermal amplification reaction in which a biological sample containing template DNA contains DNA that is diagnostic for the presence corn event MON89034 in the sample, produces a DNA amplicon diagnostic for corn DNA other than corn event MON89034 DNA (independent of whether the corn DNA is derived from non transgenic or from some other transgenic sample). Alternatively, the reaction will produce two different DNA amplicons from a biological sample containing DNA derived from a corn genome that is heterozygous for the allele corresponding to the inserted DNA present in transgenic corn event MON89034. These two different amplicons will correspond to a first amplicon that is derived from the wild type corn genome locus, and a second amplicon that is diagnostic for the presence of corn event MON89034 DNA. A sample of corn DNA that gives rise only to a single amplicon corresponding to the second amplicon described for the heterozygous genome is diagnostic for the presence of corn event MON89034 in the sample and is diagnostic for determining that the corn DNA used as template arise from a corn seed that is homozygous for the allele corresponding to the transgenic corn event MON89034 inserted DNA. The controls for this analysis should include a positive control from homozygous and heterozygous corn containing event MON89034 DNA, a negative control from non-transgenic corn or any other transgenic variety of corn, and a negative control that contains no template DNA. This assay is optimized for use with a Stratagene Robocycler, MJ Engine, Perkin-Elmer 9700, or Eppendorf Mastercycler Gradient thermocycler. Other methods and apparatus known to those skilled in the art that produce amplicons that identify the zygosity of the progeny of crosses made with MON89034 plants is within the skill of the art.

TABLE 3

Zygosity assay reaction solutions

| Step | Reagent | Amount | Comments |
|---|---|---|---|
| 1 | Nuclease-free water | add to 5 μl final volume | — |
| 2 | 2X Universal Master Mix (Applied Biosystems cat. # 4304437) | 2.5 μl | 1 X final concentration |
| 3 | Primers SEQ ID NO: 6, and SEQ ID NO: 7 (resuspended in nuclease-free water to a concentration of 20 μM) | 0.05 μl | 0.25 μM final concentration |
| 4 | PB880 SEQ ID NO: 14 Primer 6FAM ™ (resuspended in nuclease-free water to a concentration of 10 μM) | 0.01 μl | 0.4 μM final concentration |
| 5 | PB2931 SEQ ID NO: 15 Primer VIC ™ (resuspended in nuclease-free water to a concentration of 10 μM) | 0.01 μl | 0.15 μM final concentration |
| 6 | REDTaq DNA polymerase (1 unit/μl) | 1.0 μl (recommended to switch pipets prior to next step) | 1 unit/reaction |
| 7 | Extracted DNA (template): Samples to be analyzed (individual leaves) | 2.0 μl 4-80 ng of genomic DNA | Diluted in water |
|  | Negative control | 4 ng of non-transgenic corn genomic DNA |  |
|  | Negative control | no DNA template (solution in which DNA was resuspended) |  |
|  | Positive control | 4 ng of genomic DNA from known event MON89034 heterozygous corn |  |
|  | Positive control | 4 ng of genomic DNA from known event MON89034 homozygous corn |  |
| 8 | Gently mix, add 1-2 drops of mineral oil on top of each reaction. |  |  |

DNA amplification in a Stratagene Robocycler, MJ Engine, Perkin-Elmer 9700, or Eppendorf Mastercycler Gradient thermocycler or Applied Biosystems GeneAmp PCR System 9700 or MJ Research DNA Engine PTC-225 thermal cycler have been used successfully to conduct the following cycling parameters. When using the Eppendorf Mastercycler Gradient or MJ Engine, the cycles were conducted in the calculated mode. When using the Perkin-Elmer 9700, the cycles were conducted with the ramp speed set at maximum.

TABLE 4

Zygosity assay thermocycler conditions[a]

| No. of Cycles in Consecutive Order | Temperature and Duration |
| --- | --- |
| 1 | 50° C. 2 minutes |
| 1 | 95° C. 10 minutes |
| 10 | 95° C. 15 seconds |
|  | 64° C. 1 minute (−1° C./cycle) |
| 30 | 95° C. 15 seconds |
|  | 54° C. 1 minute |
| 1 | 10° C. soak |

[a]using Applied Biosystems GeneAmp PCR System 9700

Seed corresponding to the transgenic event MON89034 have been deposited on Mar. 28, 2006 under the Budapest Treaty with the American Type Culture Collection (ATCC), 10801 University Boulevard, Manassas, Va. 20110. The ATCC accession number or patent deposit designation is PTA-7455. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

---

What is claimed is:

1. A recombinant corn plant, seed, cell or part thereof comprising event MON89034, a representative sample of seed comprising event MON89034 having been deposited under ATCC Accession No. PTA-7455.

2. The plant part of claim 1, wherein said plant part is selected from the group consisting of pollen, ovule, flower, shoot, root, stalk, silk, tassel, ear, and leaf tissue.

3. A progeny plant of the corn plant of claim 1, wherein a cell of said progeny plant comprises event MON89034.

4. A hybrid corn plant wherein at least one parent is the recombinant corn plant, seed, cell, or plant part of claim 1, wherein a cell of said hybrid corn plant comprises event MON89034.

5. A commodity or foodstuff comprising the recombinant corn plant, seed, cell, or plant part of claim 1.

6. The commodity or foodstuff of claim 5 selected from the group consisting of ears of corn, shucked corn, corn silk, corn pollen, cracked corn, corn meal, crushed corn, corn flour, corn oil, corn starch, corn steep liquor, corn malt, corn sugar, corn syrup, margarine produced from corn oil, unsaturated corn oil, saturated corn oil, corn flakes, pop corn, ethanol or liquor produced from corn, distillers dry goods solids (DDGS), and animal feeds, cosmetics, bulking agents, and combinations thereof.

* * * * *